(12) United States Patent
Carmel et al.

(10) Patent No.: US 7,771,419 B2
(45) Date of Patent: Aug. 10, 2010

(54) BIOMEDICAL DISPERSIVE ELECTRODE

(75) Inventors: Yuval Carmel, Rockville, MD (US);
Anatoly Shkvarunets, Rockville, MD (US)

(73) Assignee: Granite Advisory Services, Inc., Bethesda, MD (US)

( * ) Notice: Subject to any disclaimer, the term of this patent is extended or adjusted under 35 U.S.C. 154(b) by 1394 days.

(21) Appl. No.: 11/203,977

(22) Filed: Aug. 16, 2005

(65) Prior Publication Data

US 2006/0074411 A1 Apr. 6, 2006

Related U.S. Application Data

(60) Provisional application No. 60/615,684, filed on Oct. 5, 2004, provisional application No. 60/615,759, filed on Oct. 5, 2004.

(51) Int. Cl.
*A61B 18/16* (2006.01)
(52) U.S. Cl. .......................................... 606/32; 606/35
(58) Field of Classification Search .............. 606/32–35
See application file for complete search history.

(56) References Cited

U.S. PATENT DOCUMENTS

| | | | | |
|---|---|---|---|---|
| 3,905,373 A | * | 9/1975 | Gonser | 606/35 |
| 4,303,073 A | * | 12/1981 | Archibald | 606/35 |
| 4,387,714 A | | 6/1983 | Geddes et al. | 128/303.13 |
| 4,770,173 A | * | 9/1988 | Feucht et al. | 607/152 |
| 5,000,753 A | * | 3/1991 | Hagen et al. | 606/32 |
| 5,114,424 A | * | 5/1992 | Hagen et al. | 606/32 |
| 5,836,942 A | * | 11/1998 | Netherly et al. | 606/32 |
| 6,053,910 A | * | 4/2000 | Fleenor | 606/32 |
| 6,971,391 B1 | * | 12/2005 | Wang et al. | 128/846 |
| 2005/0080407 A1 | * | 4/2005 | Ehr et al. | 606/32 |

FOREIGN PATENT DOCUMENTS

CA 219642 * 3/1987

* cited by examiner

*Primary Examiner*—Michael Peffley
*Assistant Examiner*—Samantha Muro
(74) *Attorney, Agent, or Firm*—Chalin A. Smith; Smith Patent Consulting, LLC

(57) ABSTRACT

Herein is disclosed a biomedical dispersive electrode which can redistribute the current in the subject body, increase subject safety, reduce the chance for burns and other tissue damage as well as discomfort experienced by subject during or after usage. Electrodes based on the principles of this invention can be made smaller than electrodes based on the principles of the prior art.

33 Claims, 20 Drawing Sheets

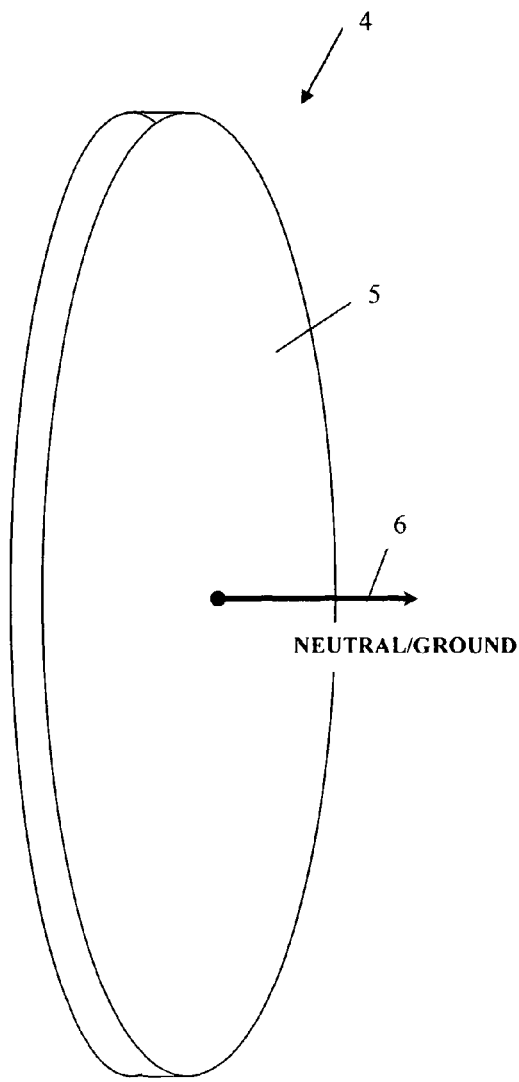
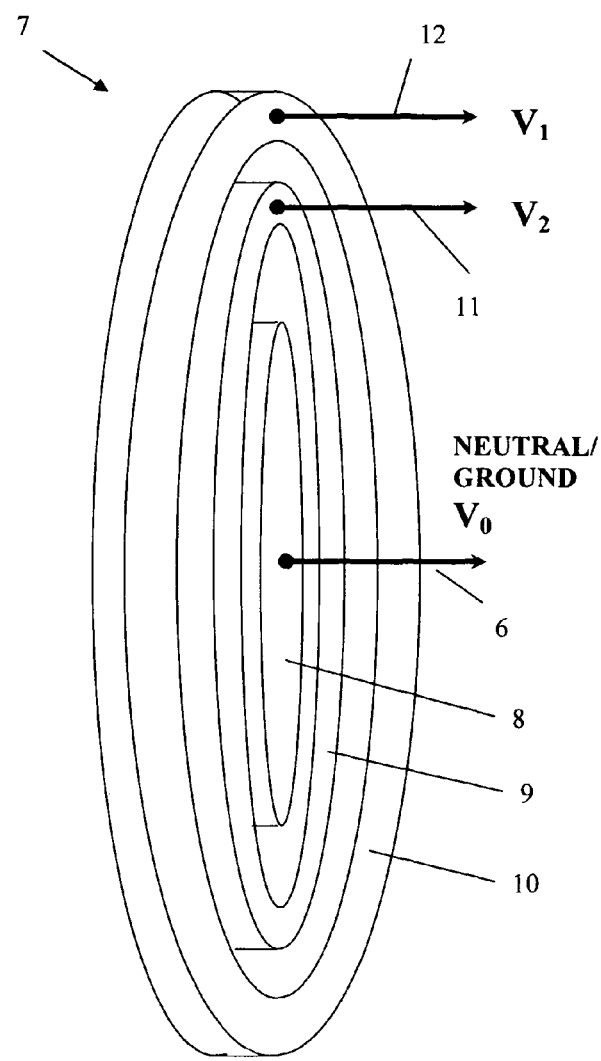
FIG. 2
FIG. 3

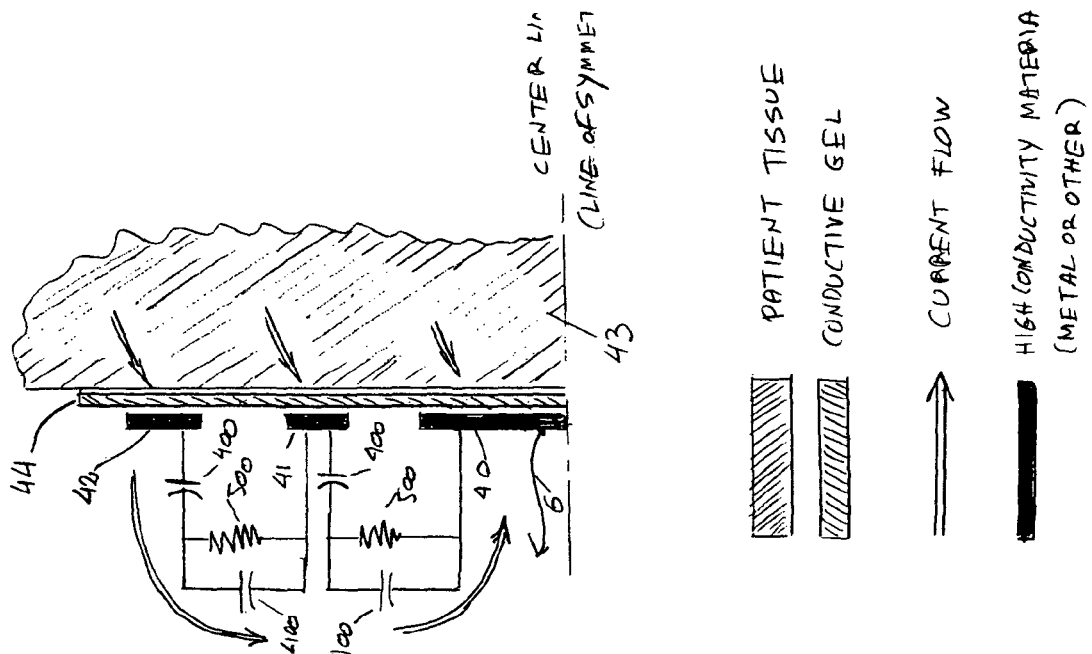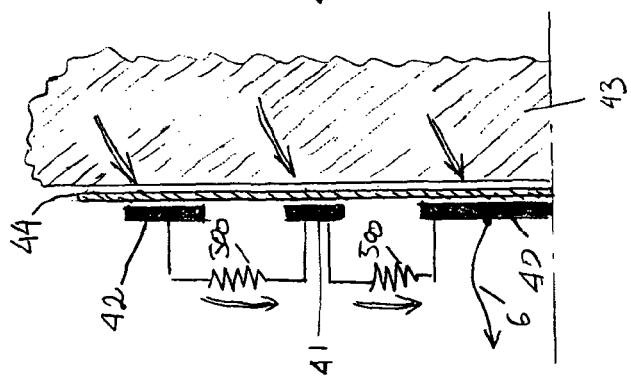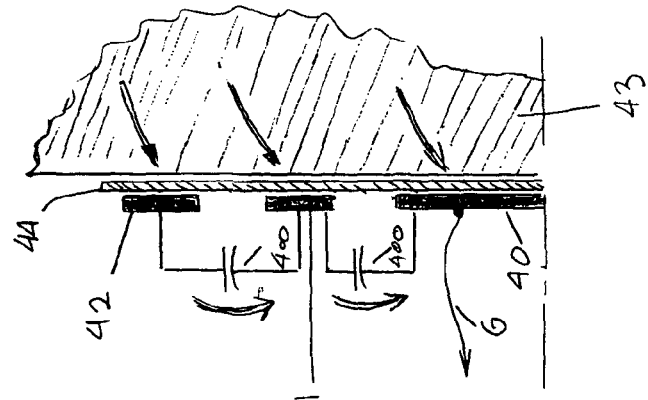

BIOMEDICAL DISPERSIVE ELECTRODE

PRIORITY

This application claims the benefit of U.S. Provisional Application Ser. Nos. 60/615,684 and 60/615,759, both filed on Oct. 5, 2004, the contents of which are incorporated by reference herein in their entirety.

TECHNICAL FIELD OF THE INVENTION

The present invention relates generally to biomedical electrodes attached to the body of a human being or an animal. These electrodes, often referred to as dispersive electrodes, return electrodes, grounding pads, patient plates or Bovie pads, are used to deliver or receive current from the body during various electrosurgical procedures such as, but not limited to, general surgery, arthroscopy, laproscopy, gastroentrology, gynecology, urology, ENT, cardiology, spinal and cosmetic surgery.

BACKGROUND OF THE INVENTION

Biomedical electrodes are used in a variety of medical and veterinary applications and are configured to operate according to the amplitude, duration, type and direction of the current flowing into or out of the body of the subject. In monopolar electrosurgery, as in all situations where electrical current is flowing, a complete circuit must be provided to and from the current source. For example, a current that enters the body at the location where the electrosurgical procedure is being performed leaves it in another place and returns to the electrical generator. It is clear that when current of enough intensity to deliberately cut, ablate, heat or stimulate is brought into contact with the body of a subject in one location, great care must be taken to ensure that unintentional damage is not done to the subject at the place where the current is leaving the body. An electrode attached to the subject's body performs the task of collecting the current safely. This electrode is supposed to perform this task by providing a large surface area through which the current can pass. When the collected current is spread over a large area, the current density is low enough so as to render the process harmless to the subject. This electrode is often referred to as a dispersive electrode, return electrode, electrosurgical pad, electrosurgical plate, grounding pad subject plate, subject return electrode or Bovie plate. These return electrodes are used in many medical procedures, including, but not limited to, monopolar electrosurgery, arthroscopy, urology, gynecology, laproscopy, open surgery, cardiac defibrillation, heating and many others. The electrodes are available commercially from such vendors as ConMed Corp., Valleylab (div of Tyco), Minnesota Mining and Manufacturing (3M), Erbe, Bovie Medical, Megadyne as well as others.

In many monopolar electrosurgical applications, radio frequency (RF) power is delivered to the field of surgery by a surgical electrode or probe. The probe strongly focuses the RF current/power in a small contact area in the vicinity of the metallic tip of the probe and in the tissue in contact with it (often less than few square millimeters). As a result, the desirable effect of heating, coagulation, ablation, cutting etc. takes place in this small area. The probe is connected to the "output" of the electrical generator by an insulated wire which, in many cases, goes through the subject body. The return current conductor is connected to the "ground" or "return" terminal of the generator through a large area electrode placed on the surface of the subject body. This electrode collects the current induced in the subject body.

In electrosurgery, it is essential that the RF power be strongly focused in the immediate vicinity of the location where the desired procedure is performed. Not less important is a strong defocusing or dispersion of the electrical current beyond the target point of the surgery. This strongly dispersed current, or "return current", should go through the subject body without harmful effects; for example, heating above a safe level can possibly lead to burns. Eventually all current is collected by the large area (on the order of few hundred square centimeters) electrode (i.e., the dispersive electrode) attached to the surface of the subject body and returned to the electrical generator by an insulated "ground" wire. Peak current density collected by the return electrode is affected by the current distribution over the area of that electrode. The distribution of the "return" current over the area of the dispersive electrode is affected, among other things, by the location of the surgical area with respect to the location of the dispersive electrode, the dispersive electrode area, and by the physical size of the subject's body between these areas. Many cases of the calculated non-uniform current density distribution under biomedical electrodes are described in the literature (e.g., Vessela Tz Krasteva et al., "Estimation of the current density distribution under electrodes for external defibrillation", Bio-Medical Engineering Online Journal, 16 Dec. 2002). Subject's safety is achieved by dispersing the "return" current over the large surface area of the return electrode.

Accordingly, it is extremely difficult, but very important, to ensure that the current density distribution in the proximity of the dispersive electrode be as uniform (homogeneous) as possible. Since the return electrode is usually placed on the surface of subject's body, the cross section of the return current channel (i.e., the physical size of the subject's body) is sharply and abruptly decreased to the size of the dispersive electrode itself at the position where the electrode is attached to, and in contact with, the body. As a result, the dispersive electrode always compresses, or focuses, the return current in its vicinity. In all cases, unless special corrective measures are taken, the collected current distribution over the area of the return electrode is different from the desired uniform, smooth distribution. The result is that an extremely non-homogeneous distribution exists on the surface of the dispersive electrode, and in the proximity of the electrode below its surface (in the subject's body). Often current density near the outer edge of the dispersive electrode may be 10 times higher than at the center. In practice, this means that undesirable heating of the subject's body is strongly enhanced in the proximity of the outer edge of the dispersive electrode; this is often called the "edge effect". The tendency of electrosurgical return current to cluster and generate heat in the vicinity of the corners and the outer edges of the return electrodes has been a long-standing design/safety problem that can lead to subject burns. Because of this inefficient current distribution, safety consideration have dictated that:

(a) Return electrodes must be much larger than necessary so as to provide homogeneous current distribution (i.e., the physical area of the electrode must be much larger than its "effective" area), and (b) Most return electrodes must be positioned on the subject body with the long edge facing the surgical site to avoid burns.

Dispersive electrodes are also used for external defibrillation. Defibrillation of the heart is a widespread and well-established procedure for resuscitation of cardiac arrest victims. The most accessible approach for electrical cardiac therapy is via external electrodes, placed on selected locations on the surface of the thorax. The electrodes have a large surface area, and provide the high, and supposedly uniform, current density distribution in the heart needed for excitation of most myocardial cells, thus forcing them to return to normal rhythm. However, it has been reported that with conventional electrodes about 25% of the myocardium volume could be subject to current densities more than four times higher than the threshold density. Another aspect of the problem is the predominance of high current density along the perimeter of defibrillator electrodes applied on human skin (same edge effect discussed earlier). This can lead to unwanted damage and even severe skin burns or electroporation.

As current density is highly non-uniform across the return electrode, and is very high close to its edge, there is a risk of burns due to the tendency of the current and heat to cluster at the edges of the return electrode. Therefore, for safety reasons the pads are made much larger than needed. However, the larger the pad, the more difficult it is to place on subjects with limited muscle tissue, especially the elderly, babies and children. Suitable pad placement on burn victims and subjects with implants, excessive hair, scar tissue or skin problems has also proven to be difficult.

Accordingly, it is readily apparent that the art needs biomedical return electrodes capable of reducing the "clustering" of current at the edges of the electrode. The present invention solves the problems discussed above by providing a novel biomedical return electrode in which the current density distribution in the proximity of the dispersive electrode is much more uniform. In particular, the electrodes of the present invention are capable of altering and greatly improving the uniformity of current density profile in the proximity of the interface between the electrode and mammalian tissue. As a result, the chance for burns and other tissue damage to the skin as well as discomfort experienced by subject during or after usage is reduced.

In sum, the present invention provides a biomedical dispersive electrode which favorably redistributes the current in the subject's body in the proximity of the interface between the electrode and subject tissue, increases subject safety, and reduces the chance for burns and other tissue damage as well as discomfort experienced by subjects during or after usage. This new approach makes it possible to substantially reduce the size of the electrode, without compromising subject safety. Smaller size will improve the ease of use required in subject care environment.

SUMMARY OF THE INVENTION

The present inventors discovered that reshaping and splitting the electrically conducting component into multiple components of various, specially designed configurations resulted in a favorable current redistribution in the subject body. This goal is achieved since the combination of multiple electrically conducting components of the device, the conductive dielectric, as well as the electrical properties of the subject tissue are all integrated as part of an equivalent electrical circuitry. With proper design, discussed in detail below, the result is that the current distribution in the subject body can be "tailored" as needed for a specific use or application. In some applications, a favorable condition is created by a homogeneous current density distribution. In other applications, a specially tailored non-homogeneous current density can be advantageous.

The electrical circuitry that allows the favorable redistribution of the current in the subject body can be composed of passive, active, lumped, distributed, internal or external components, and includes the tissue of the subject.

Accordingly, in the biomedical electrode of the present invention the current distribution over the electrode is controlled in a unique way by using an advanced electrode design. The return current distribution in the proximity of the electrode is affected by the voltage (active, or passive) distribution applied along the surface of the electrode. Herein, the term "passive" means that the desired voltage is self-generated by the current flowing through the return electrode assembly in contact with the subject. Conversery, the term "active" means that the voltage is supplied externally. For illustration purposes, consider the case where the return electrode is not a solid material of high conductivity, like metal, but rather consists of multiple metallic components, or segments, electrically connected in a defined way according to the principles of this invention. Properly chosen passive or active voltage distribution can be used to "tailor" the current density distribution in a desired way, e.g., to redistribute current nearly homogeneously over the surface of the return electrode. In the context of the present invention, it is important to properly design a favorable voltage distribution. Non-favorable voltage distribution in a multi component dispersive electrode can substantially worsen, instead of improve, the current density distribution compared to a commonly used dispersive electrode.

As indicated, smoothing the current distribution over the surface of the biomedical return electrode can be achieved by creating a favorable voltage distribution. Herein, the present invention provides three different approaches for the implementation of these concepts: category (1)—passive resistive-capacitive dividers; category (2)—passive resistive-inductive dividers, and category (3)—active voltage distributors. The implementation of these three principles, or combinations of these principles, will result in many versions of electrodes according to the principles of this invention, as will be described below.

Accordingly, following the passive resistive capacitive divider approach of category (1), the present invention provides a metallic electrode that, instead of being a single conducting plate (or two in the case of a split-pad), is mechanically and electrically divided into multiple elements, such as rings or other combinations of metallic electrodes (i.e., a multi element/segment return pad). These conductive elements or conductors are electrically incorporated into a voltage divider in the form of distributed or lumped resistors, capacitors, or combinations thereof, including a conductive dielectric adhesive (sometimes referred to as a gel) as a resistive-capacitive element. Note that conductive dielectric materials of various kinds are well known for those skilled in the art, and are widely used in order to create good contact between the biomedical electrode and the body of the subject.

In use, a return wire (ground/neutral) is connected to one or more of the central elements of the electrode. In the present invention, the voltage induced on the periphery elements increases as you move farther away from the center element. A resistive-capacitive voltage divider according to the principles of this invention will redirect the return current towards the center of the electrode, thus creating the desired more uniform and homogeneous current distribution over the entire area of the biomedical electrode.

The resistive-capacitive connection can be provided, for example, by appropriate use of distributed-circuit-elements, such as conductive/dielectric layers (conductive gel or some other conducting material including metallic foil) placed on the subject side or the opposite side of the dispersive pad; by appropriate use of lumped (discrete) circuit elements; or by combinations of these approaches. Note that the subject tissue itself can be described as a conductive dielectric, and is "included" into the equivalent electrical circuitry of the voltage divider.

Many variations are possible according to the principles of this invention, and illustrative examples are described in detail below. All are designed to create more optimal voltage and current distribution in the subject body and therefore increase subject safety. Examples of dispersive electrodes according to the present invention include, but are not limited to single and split-pads; circular and non-circular; symmetric and non symmetric; disposable and non-disposable.

Note, herein a dispersive electrode is referred to as a "split-pad" when it constructed in a way that allows for the measurement of the quality of contact impedance between the pad and the patient body. Alternatively, when the dispersive electrode is not constructed in such a way, it is referred to as non-split or single pad. A split-pad can be implemented by adding an additional conducting electrode, or by cutting the conducting electrodes of a non-split pad (thus doubling the number of conducting electrodes). In the figures, the non-split pads are often shown schematically with a conducting wire connection, while the split-pads are often shown with two conducting wires.

In another embodiment, the present invention provides a dispersive electrode that facilitates the creation of a favorable voltage distribution in the subject's body below the conducting element of the electrode, rather than on the electrode itself. This is done by using a continuous metallic electrode (non-segmented) and controlling the thickness and or the conductivity of the conductive dielectric layer situated between the metallic component of the dispersive pad and the subject's skin.

Following the resistive-inductive divider approach of category (2), the present invention provides a dispersive electrode comprising, for example, a return electrode shaped in the form of flat, multi-turn spiral. This construction has intrinsic self-inductance that can function as an inductive voltage divider. When current is collected on this style of dispersive electrode, a voltage distribution is self-generated along the surface of the electrode (between the turns of the spiral). When the ground wire is connected to one or more electrodes at the center of the spiral, the voltage increases from the center to the edge of the spiral. This voltage increase redistributes the return current away from the edge and toward the center, thus creating a more homogeneous current distribution.

Many variations to the dispersive electrodes designed according to the principles of (2) above are possible. For example, the electrode may comprise a solid central area surrounded by a spiral in the periphery. Other variations include, but are not limited to, single and split-pads; circular and non-circular; symmetric and non-symmetric; disposable and non-disposable, spiral; non-spiral (ring) and more. The resistive-inductive connection can be provided, for example, by appropriate use of distributed circuit elements like conductive dielectric layers (conductive gel or some other conducting material including metallic foil), or lumped (discrete) circuit elements placed on the subject side or the opposite side of the dispersive pad; or by combinations of these approaches. Furthermore, the lumped element approach can be used effectively with the two other categories according to the principles of this invention (namely the resistive-capacitive and the active).

Following the active voltage distribution approach of category (3), the present invention provides a dispersive electrode comprising an active voltage distributor. In this embodiment, the favorable voltage distribution on the return electrode is created by supplying voltages from external sources.

Accordingly, one aspect of the present invention involves the use of distributed, or lumped, resistive components, capacitive components, inductive components, or a combination thereof, to alter and greatly improve the uniformity of current density profile in the proximity of the interface between the electrode and mammalian tissue.

Another aspect of the present invention involves the selection of geometrical configurations, shapes and materials to alter and greatly improve the uniformity of current density profile in the proximity of the interface between the electrode and subject tissue.

Another aspect of the current invention involves dividing of the metallic, electrically conductive portion of the biomedical electrode into multiple conductive elements, in order to redistribute the current in the subject body.

Thus, it is an object of the present invention to provide a biomedical electrode, comprised of multiple electrical conductors in contact with a conductive dielectric material (conductive gel) that interfaces the subject for exchanging electromagnetic energy. The conductive dielectric preferably takes the form of a thin layer of variable geometry, including, but not limited to, circles, ellipses, polygons, and combinations thereof, both linear and non-linear. Furthermore, the outer edges of the conductive dielectric layer may comprise a series of curves or waves, having, for example, a sinusoidal configuration. Note, the outer edges of the conductive dielectric layer may extend beyond the perimeter defined by the electrical conductors.

Another object of the present invention is to provide a more universal biomedical electrode that can be used effectively and safely for large variety of subject population, such as babies; children; adults; the elderly; subjects with excessive hair, limited muscle tissue, scar tissue or skin problems, and burn victims that normally proved very difficult. An advantage of this aspect is the reduction in the required inventory of electrodes in medical care facilities.

Another object of the present invention is to provide a biomedical electrode having a small size. Because of its ability to disperse the current more uniformly, most of the area of an electrode of the present invention is utilized effectively. At present, return electrodes must be much larger than necessary if the current distribution is to be made homogeneous (in other words, the "effective" area is much larger than its physical area). Electrodes according to the principles of this invention are characterized by an "effective area" that is roughly equal to the geometrical area of the electrode.

Another object of the invention is to provide a biomedical electrode for electrosurgical applications that has a maximum rise in temperature of less than 6° C. from beginning of use with an electrosugical generator, when methodology according to industry testing standard AAMI Standard HF18 (American National Standard for Electrosurgical Devices, Maximum safe temperature rise).

Another object of the invention is to provide a biomedical electrode characterized by a more uniform temperature distribution profile as compared to electrodes based on known art.

An advantage of the biomedical electrode of the present invention is its ability to reduce the chance for burns and other tissue damage to the skin during or after usage in electrosugery.

Another advantage of the biomedical electrode of the present invention is its ability to reduce the pain, irritation and discomfort experienced by subjects during and after removal of the electrode from the subject skin because the electrode is generally smaller than electrodes based on known prior art.

Another advantage of the biomedical electrode of the present invention is its ability to be positioned on the subject body without special regards to orientation relative to the surgical site.

Accordingly, in one preferred embodiment, the dispersive electrode of the present invention is comprised of an electrically non-conductive backing, and at least one, and in many cases more than one, conductive plates with a configuration and shape as shown, for example, by some of the embodiments of this invention. The plates will most often be adhered to the electrically non-conductive backing. In addition, a layer of conductive dielectric material, such as a conducting gel, is preferably disposed between the conductive plates and the surface of the electrode in contact with the body of the subject. A film of conductive adhesive may be present in contact with the conductive plate(s) and the gel like material. In some cases, it may be advantageous to place the conductive dielectric material on both sides of the conductive plates. As noted above, in some embodiments, the conductive dielectric gel-like material may extend beyond the outer edges of the metallic plate(s). Note, the outer edges the metallic plates may comprise a curvilinear or waved-edge configuration.

Another aspect of this invention involves the use of electrically insulative (non-conductive) material for the backing. The electrically non-conductive backing material is preferably comfortable to the various contours of the subject body. Many materials can be used for this purpose, as will be apparent to those skilled in the art.

For electrosurgical applications, the conductive adhesive can serve three purposes. First, it serves to adhere and create intimate contact between the biomedical electrode and the body of the subject. Second, it provides for transfer of the electrosurgical current into and out of the subject body. Third, it provides for transfer of the current in a way which permits the electrode to register an alarm condition (CQM) if a portion of the electrode unpeels from contact with the body of the subject.

All the advanced pads according to the principals of this invention are characterized by high efficiency (i.e., the physical area is approximately equal to the effective area), high current carrying capabilities and small surface area as compared to standard electrosurgical pads. As such, the pads can be used by adults, children and babies while maintaining subject safety.

While the invention has been described with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. For example, the pads can take the shape of various geometries beyond those described in the figures; the edge of the conducting material can take the form of wiggles or corrugations both on the inside and outside, segmented electrode and segmented conductive dielectric with different electrical and thermal properties at each segment or section; as well as other forms without deviating from the scope of this invention.

BRIEF DESCRIPTION OF THE DRAWINGS

FIG. 2 depicts an example of a prior art single (non-split) return electrode.

FIG. 3 depicts an example of an active voltage distributor return electrode according to the present invention.

FIG. 4 is a diagram of the electrical circuit of a passive capacitive voltage divider dispersive electrode according to the present invention.

FIG. 5 is a diagram of the electrical circuit of a passive resistive voltage divider electrode according to the present invention.

FIG. 6 is a diagram of the electrical circuit of a passive resistive-capacitive voltage divider according to the present invention.

DETAILED DESCRIPTION OF THE PREFERRED EMBODIMENTS

Figure 1:
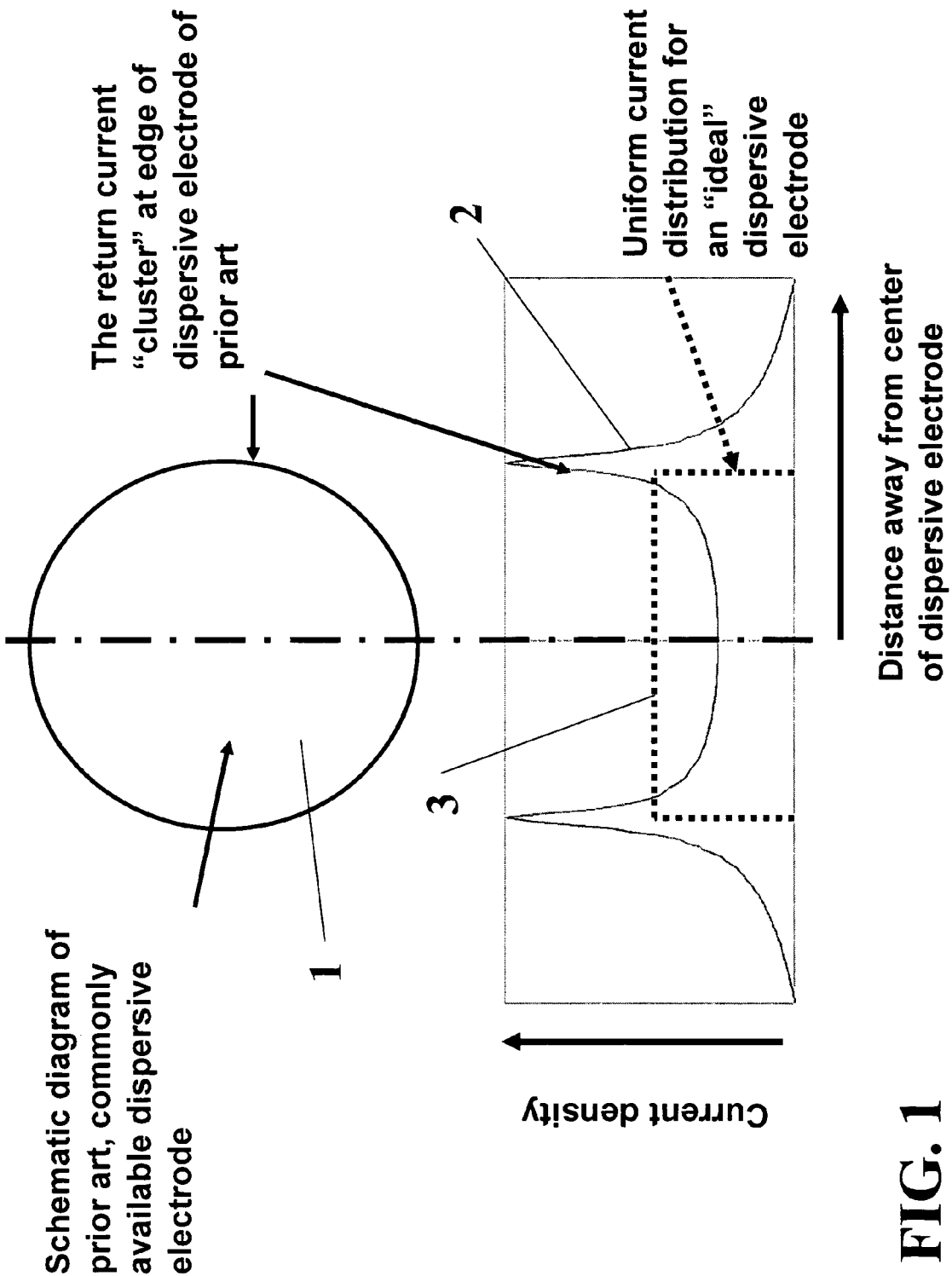
FIG. 1 is an illustration showing the calculated, highly non-uniform current density distribution over a conventional circular return electrode having an area of ~80 cm² and that of an "ideal" return electrode.

The words "a", "an", and "the" as used herein mean "at least one" unless otherwise specifically indicated.

The biomedical electrodes of the present invention have both medical and veterinary applications. Accordingly, the term "subject" as used herein refers to both humans and animals, more preferably mammals.

Unless otherwise defined, all technical and scientific terms used herein have the same meaning as commonly understood by one of ordinary skill in the art to which this invention belongs. In case of conflict, the present specification, including definitions, will control.

Hereinafter, reference is made to the accompanying drawings which form part thereof, and in which is shown, by way of illustration, specific embodiments in which the invention may be practiced. These embodiments are described in sufficient detail to enable those skilled in the art to practice the invention, and is to be understood that other embodiments may be utilized, and that structural, logical and electrical changes may be made without departing from the spirit and the scope of the present invention. Referring now to the drawings, like elements are designated by like reference numerals when appropriate.

FIG. 1 shows, as an example, the calculated, highly non-uniform current density associated with a circular pad 1 having an area of about 80 $cm^2$. The tendency of the return current to cluster, and heat the subject, at the edges of the return electrode (also known as "edge effect") has been a long-standing problem that can lead to subject burns. This calculated "clustering" 2 is shown in the figure. Also shown as a dotted line, for illustration purposes, is a hypothetical, ideal, uniform current distribution 3. To overcome the overheating in the areas of current "clustering", the return electrodes must be much larger than necessary if the current distribution is to be made homogeneous.

FIG. 2 shows, for illustration purposes, a schematic perspective view of a conducting plate 5 of a single (non-split) return electrode 4 having a circular geometry based on known art. Also shown is the electrical wire 6 connecting the electrode to the ground, or neutral, of the electrical generator or to a sensing unit. For clarity, other elements needed for proper operation are not shown in this figure. Those elements and other features will become apparent in the discussion follows.

For illustration purposes only, FIG. 3 shows a schematic, perspective view of a four component (three rings and a central conducting plate) of a single (non-split) return electrode 7 according to the principles of active voltage distribution. The central conducting plate 8 is connected to the ground of the electrical generator through wire 6. A conducting plate in the form of a ring 9 is connected to the external voltage source through electrical wire 11. Another conducting plate in the form of a second conducting ring 10 is connected to an external voltage source through electrical wire 12. In the case of externally generated active voltage distribution, the external voltage sources should be synchronized with the main electrical generator. Other electrode configurations are contemplated by the present invention. For example, the electrode may be provided with more or less conducting rings and segments. For clarity purposes, other elements required for proper device operation are not shown in this figure. These additional elements and other features will become apparent in the discussion follows.

FIG. 4 shows a schematic diagram of one half (around a line of symmetry) of the equivalent electrical circuit of a passive capacitive voltage divider (category (1)). Shown in this figure is a cutaway of a three-component geometry (two-rings and a conducting plate). The central conducting plate 40, as well as the conducting rings 41 and 42 are attached to the subject tissue 43 through an interface, or intermediate layer, or field of conductive dielectric material 44. In this example of a non-split pad, the device is connected to an external electrical generator through an electrical wire 6. The capacitive elements 400 can be distributed or lumped.

FIG. 5 shows a schematic diagram of one half (around a line of symmetry) of the equivalent electrical circuit of a passive resistive voltage divider (category (1)). Shown in this figure is a cutaway of a three-component geometry (two-rings and a conducting plate). The central conducting plate 40, as well as the conducting rings 41 and 42 are attached to the subject tissue 43 through a field of conductive dielectric, gel-like, material 44. In this example of a non-split pad, the device is connected to an external electrical generator through an electrical wire 6. The resistive elements 500 can be distributed or lumped, external or internal.

FIG. 6 shows a schematic diagram of one half (around a line of symmetry) of the equivalent electrical circuit of a combination passive capacitive-resistive voltage divider.

Shown in this figure is a cutaway of a three-component geometry (two-rings and a conducting plate). The central conducting plate 40, as well as the conducting rings 41 and 42 are attached to the subject tissue 43 through a field of conductive dielectric, gel-like, material 44. In this example of a non-split pad, the device is connected to an external electrical generator through an electrical wire 6. The capacitive 400 and resistive 500 elements can be distributed or lumped.

The embodiments shown in FIGS. 4, 5 and 6 can be also be implemented as a split-pad version, which permits the electrode to register a detection system of a CQM alarm condition if a portion of the electrode unpeels from contact with the body of a mammalian subject. The conductor plates 40, 41, 42 are conveniently made of metal, preferably in the form of a foil. However, other conventional conducting, non-metal materials are also contemplated. In addition, although the figures depict a device that is cylindrically symmetric around the centerline, other embodiments are contemplated. For example, the geometries can be rectangular, elliptical, polygonal or many other shapes, both symmetric and non-symmetric, without deviating from the spirit of this invention.

As indicated, the conducting plates may be attached to the subject tissue 43 through an intermediate interface layer, or multiple layers, of a field of conductive dielectric material 44. Many compositions for this material are known and available for use by people experienced in the art. Non-limiting examples useful in connection with the present invention include various compositions made by U.S.-based companies like ConMed, Tyco-Valleylab, Minnesota Mining and Manufacturing, Bovie Medical as well as European companies such as Erbe, as well as others in China and Korea. An important property of these conductive dielectric materials is their specific electrical resistivity (which is defined as the inverse conductivity). Some non-limiting examples of the specific electrical resistivity of various known and used material compositions 44 are given in Table 1. The field of conductive dielectric material, in a form of one or more intermediate interface layers, itself acts as the distributed element described in the equivalent circuit of FIGS. 4, 5, and 6. In other cases, devices based on the principles of this invention can be used with or without additional lumped elements shown in the equivalent circuits described above. Furthermore, the embodiments of FIGS. 4, 5, and 6 may be modified to be category (2) electrodes simply by replacing the capacitive components with inductive components (lumped or distributes).

TABLE 1

| Example | Specific Resistivity at 60 kHz [Ohm · m] | Specific Resistivity at 200 kHz [Ohm · m] | Specific Resistivity at 500 kHz [Ohm · m] |
| --- | --- | --- | --- |
| 1 | 5.3 | 5.5 | 5.1 |
| 2 | 160 | 130 | 98 |
| 3 | 15.1 | 16.2 | 16.1 |
| 4 | 3.1 | 3.1 | 3.1 |
| 5 | 4.8 | 4.8 | 4.7 |
| 6 | 2 | 2.1 | 2.2 |

Because of its electrical resistivity, the conductive dielectric material creates voltage distribution if electrical current is flowing through it, as is the case in electrosurgery. Also, this material dissipates electrical energy, meaning it converts current into heat or, in other words, the conductive dielectric material is electrically heated. Accordingly, it is sometimes also referred to as a dissipative material or lossy dielectric. Specific designs of devices based on the principles of this invention will take into account the specific properties of a conductive dielectric material 44, and specific dimensions will therefore depend on the properties of the materials used, among other things.

Note that the range of useful electrical resistivity is typically 0.1-200 Ohm·m, more preferably 1-20 Ohm·m. The conductive dielectric can be solid or gel-like material can be used in the form of non-uniform thickness layer, or layers, of various geometries, as will be shown in some of the illustrative embodiments that follow.

Figure 7:
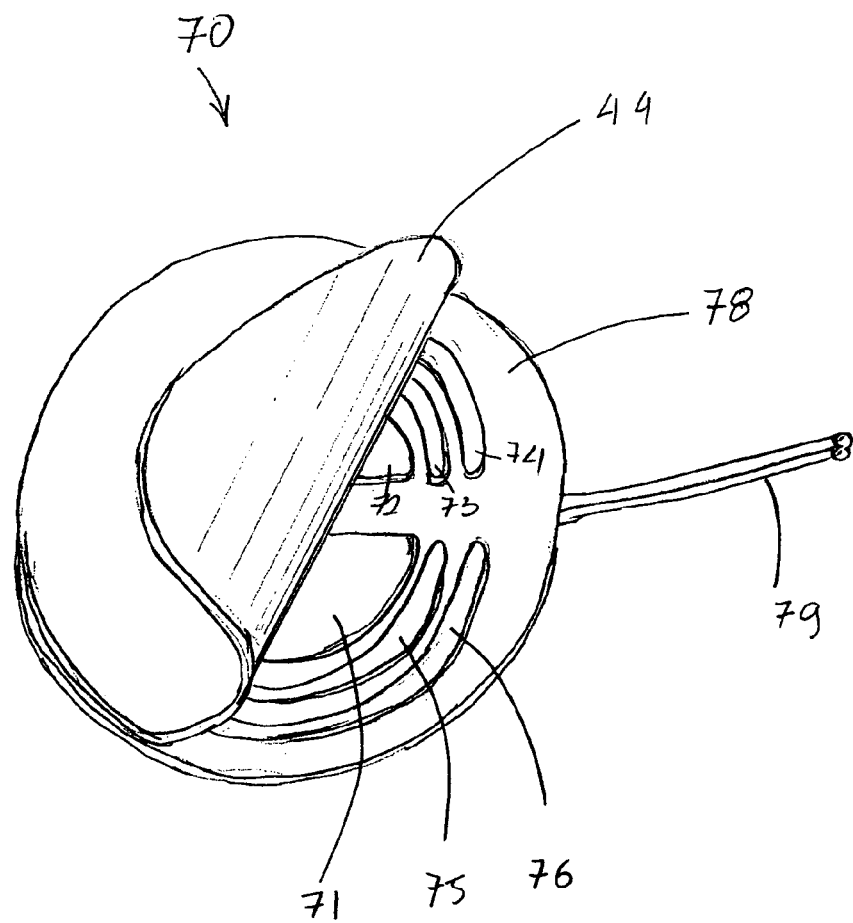
FIG. 7 depicts an example of a split pad according to the principles of category (1) of the present invention (resistive-capacitive divider). A perspective view of a symmetric (circular), two-ring (three component), split return electrode is provided. The voltage induced on the periphery components increases as you move away from the center element, thus redistributing the return current towards the center of the electrode. Numerous other shapes, including, for example, elliptical, rectangular, square, square with rounded corners and wiggled or waved edges are contemplated by the present invention.

FIG. 7 depicts a perspective view of a preferred embodiment of a dispersive pad 70 based on the principles of the present invention, category (1). It particularly shows a three-component (two-rings and central plate) split pad, where the gel-like material 44 is partly peeled off for better visualization of internal construction details. More specifically, the split inner conducting plates 71, 72, the split first conducting ring 73 and 75, and the split second conducting ring 74 and 76, all mounted on, or glued to, the pad backing material 78 suitable for protecting the device. The pad backing material 78 is electrically non-conducting. The two electrical wires, 79, are each connected to the split inner conducting plates 71 and 72. Note that only one wire is needed for a single, non-split pad, while two are needed for a split pad to form a connection to the electrical control unit, not shown. Note that for simplicity, a release liner, suitable for protecting the gel-like material during shipping and handling while releasing easily before the time of use, is not shown in FIG. 7. The material 44 will be in contact with the mammalian skin, or tissue, during use.

Figure 8:
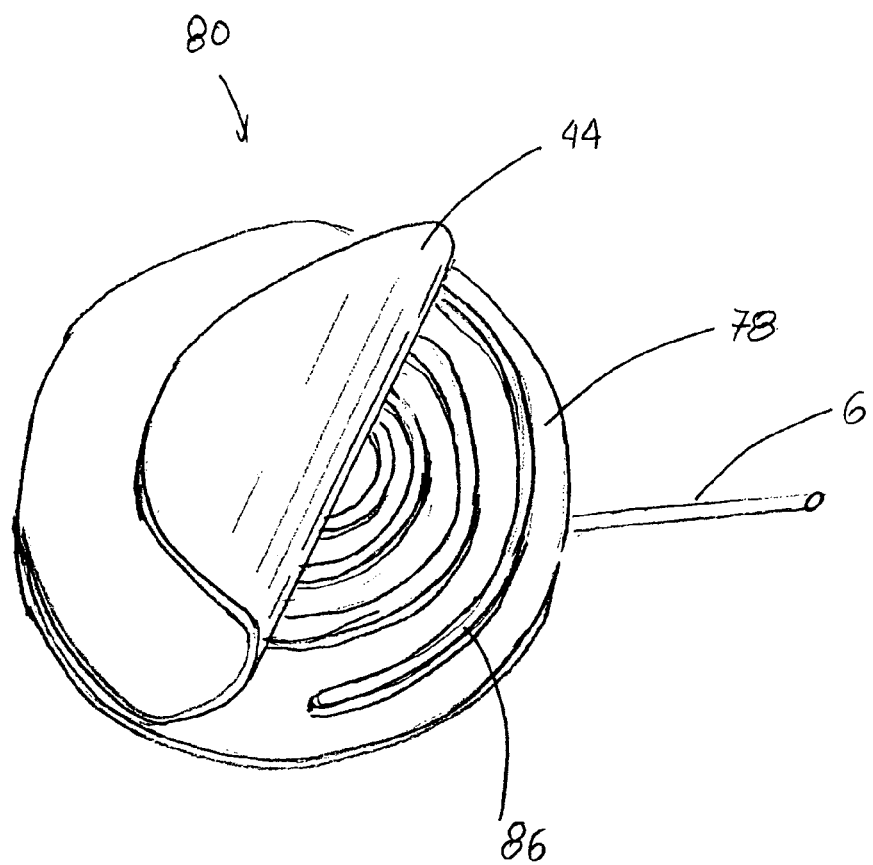
FIG. 8 depicts an example of a single (non-split) pad according to the principles of category (2) of this invention (resistive-inductive divider). A perspective view of a spiral, single (non-split) return electrode is provided. The voltage increases as you move away from the center, thus redistributing the return current towards the center of the electrode. Numerous other shapes, including, for example, elliptical, rectangular, square, polygonal, square with rounded corners and waved edges are contemplated by the present invention.

FIG. 8 is a perspective view of yet another preferred embodiment of a dispersive pad 80, based on the principles of the present invention category (2). It shows a spiral, single pad, where the gel-like material 44 is partly peeled off for better visualization of internal construction details. More specifically, the spiral conducting plate 86 mounted on, or glued to, the pad backing material 78 suitable for protecting the device. The pad backing material 78 is electrically non-conducting. The electrical wires, 6, are connected to the center of the spiral, hidden from view in this figure. Note that only one wire is needed for a single, non-split pad. Also note that for simplicity, a release liner, suitable for protecting the gel-like material during shipping and handling while releasing easily before the time of use, is not shown in FIG. 8. The liner is generally electrically non-conductive and can be made from any number of commercially available materials. The material 44 will be in contact with the mammalian skin, or tissue, during use.

FIGS. 9, 10, 11, 12, 13 and 14 illustrate four different illustrative examples of preferred embodiments according to the principles of this invention. For simplicity, the backing material 78 is omitted from these figures.

Figure 9:
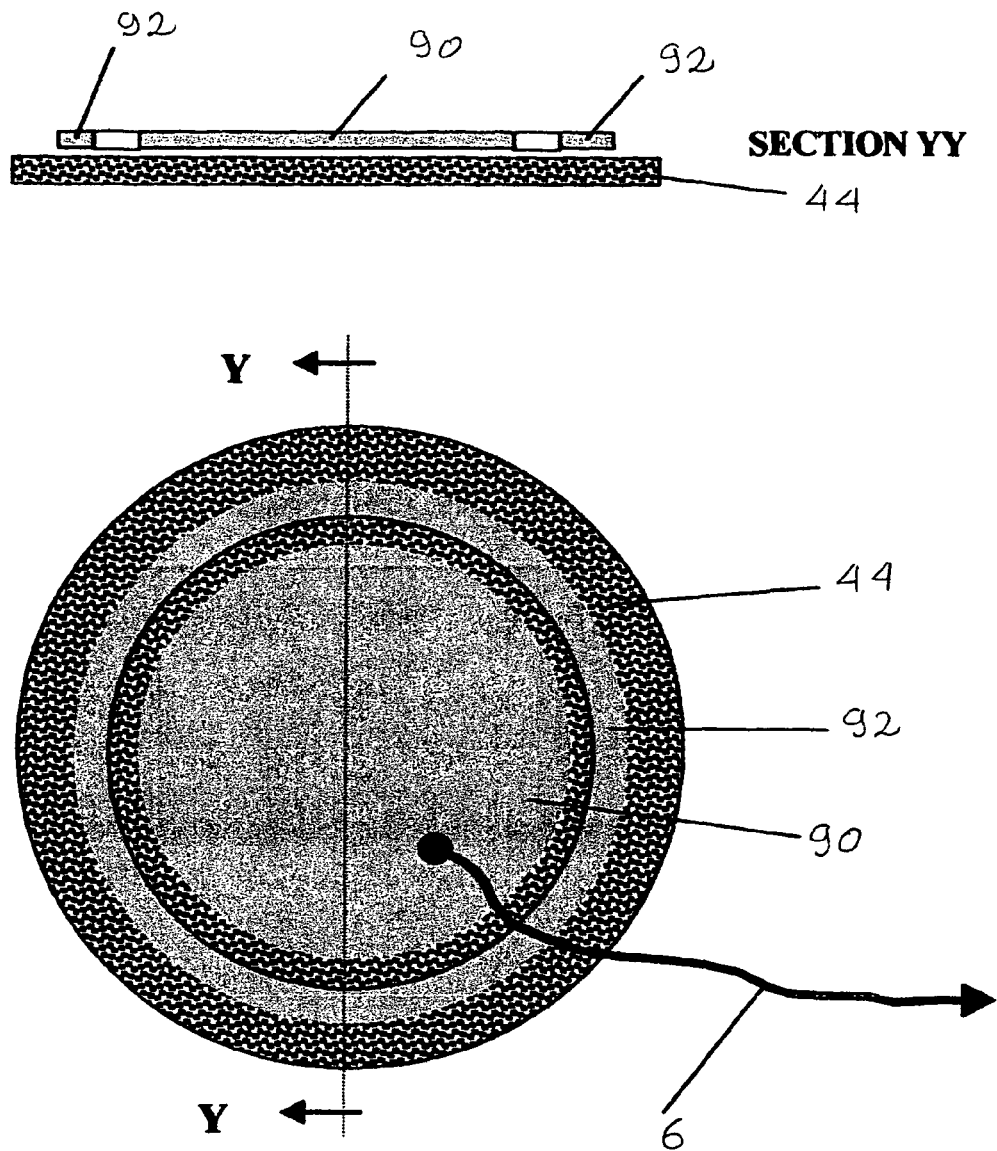
FIG. 9 provides top and cross-sectional views of another example of a resistive-capacitive divider electrode of the present invention, namely a circular two component (one central plate and one ring), single (non-split) pad.

FIG. 9 shows both a bottom view and a cross sectional view YY of one preferred embodiment of a two component (one central conducting plate, one ring), single (non-split), dispersive pad based on the principles of category (1) according to this invention. The central conducting plate 90 and one conducting ring 92 are attached to the conductive material 44 which extends radially to, or beyond, the outermost radius of the conducting ring 92. The conducting plate 90 is connected to the electrical generator (not shown) via an electrical connection 6.

Figure 10:
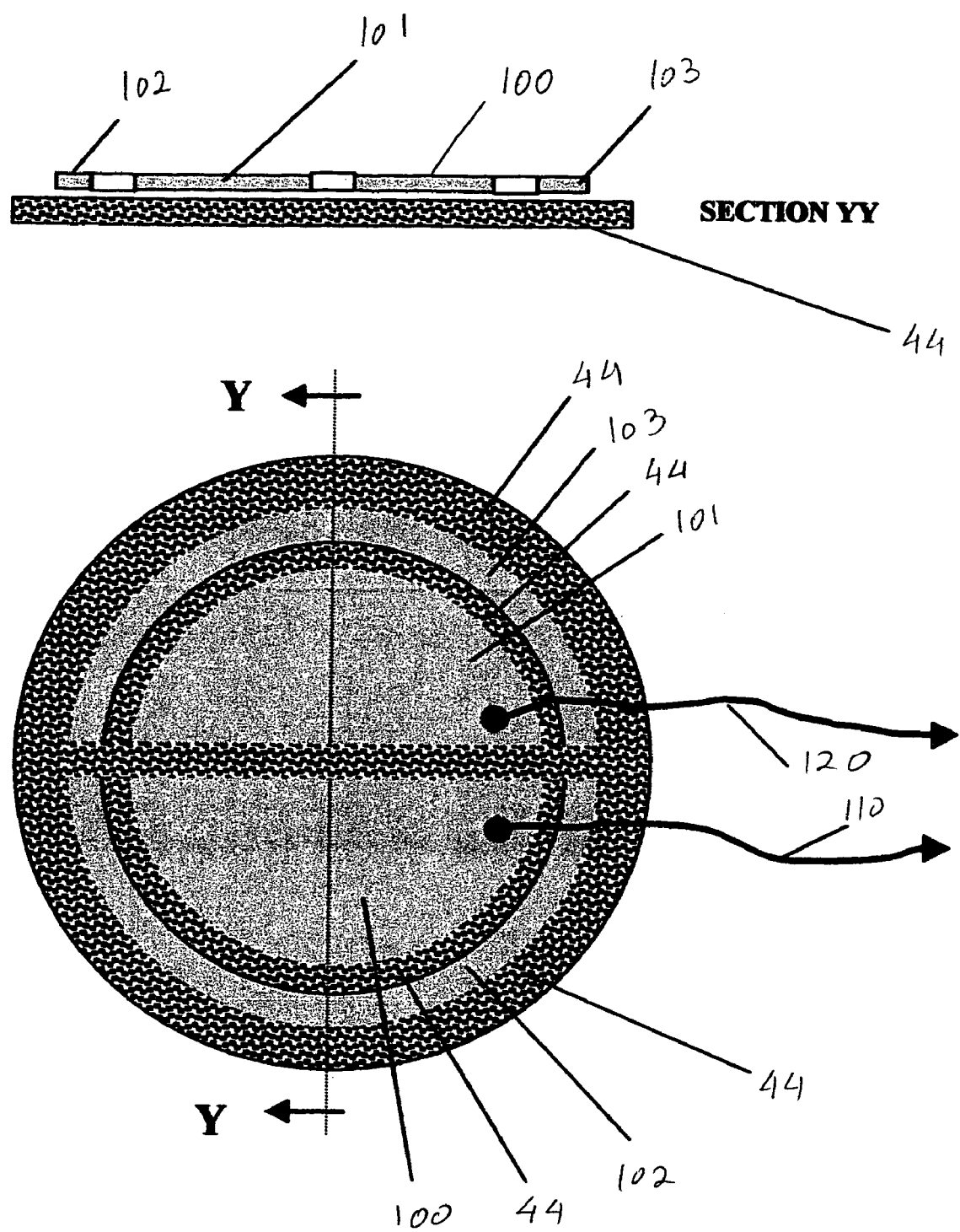
FIG. 10 provides top and cross sectional views of another example of a resistive-capacitive divider electrode of the present invention, namely a two component (one central plate and one ring), split pad.

FIG. 10 shows both a bottom view and a cross sectional view YY of a split version of the single (non-split) dispersive pad shown in FIG. 9, also based on the principles of category (1) according to this invention. In the split pad version, the central conducting plate 90 of FIG. 9 is split here into two halves 100 and 101. The conducting ring 92 of FIG. 9 is split here to two halves 102 and 103. All the conducting elements 100, 101, 102, 103 are attached, or glued, to the material 44, which extends radially to, or beyond, the outermost radius of the conducting rings 102, 103. The conducting plates 100, 101 are connected to the electrical generator (not shown) via electrical connections 110, 120 respectively.

Figure 11:
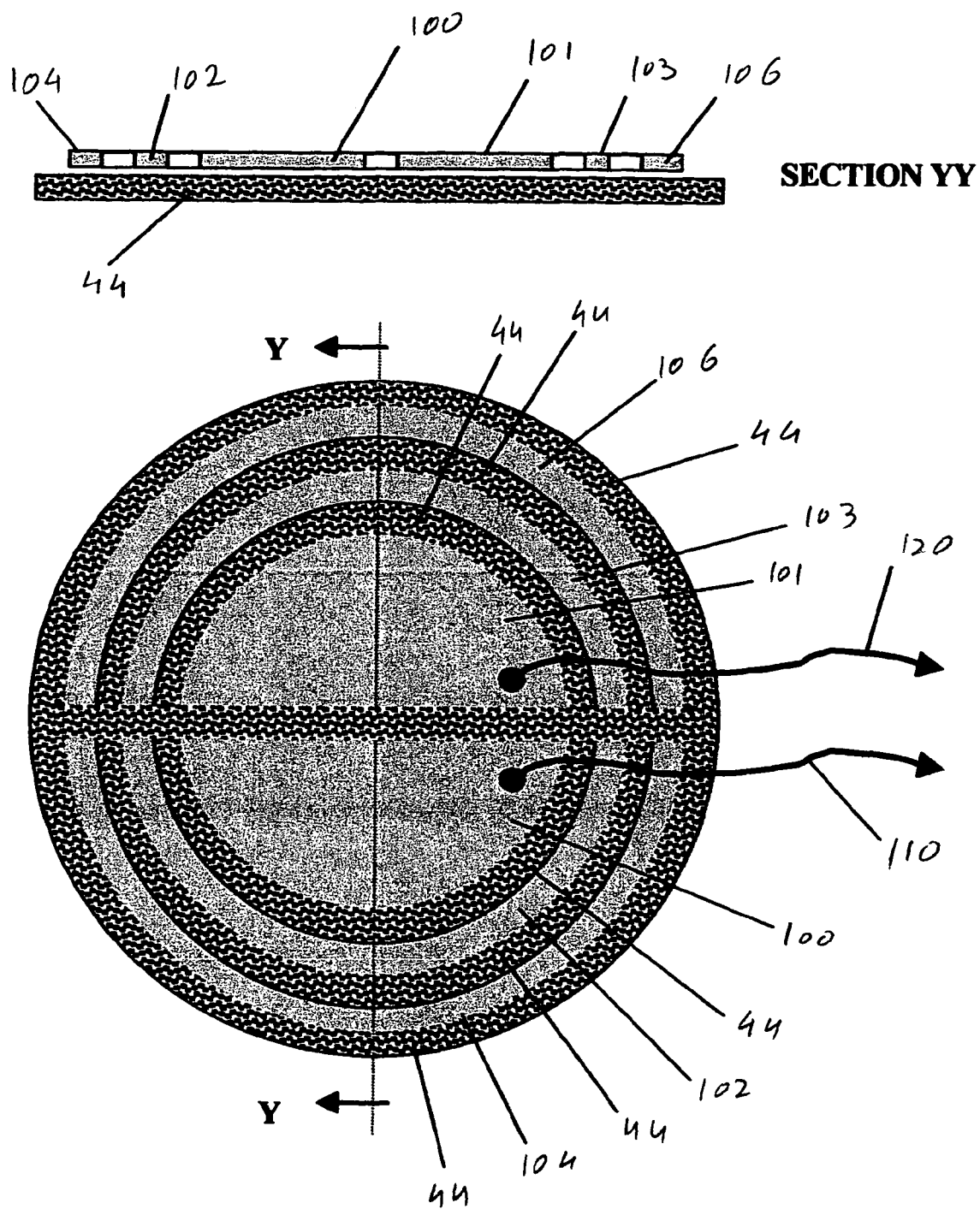
FIG. 11 provides top and cross sectional views of another example of a resistive-capacitive divider electrode of the present invention, namely a circular three component (one central plate and, two rings), split pad.

FIG. 11 shows both a bottom view and a cross sectional view YY of a split version of three component, two ring dispersive pad, also based on the principles of category (1) according to this invention. In the split pad version shown, the central conducting plate is split here into two halves 100 and 101. The first conducting ring is split into two halves 102 and 103, and the second conducting ring is split into two halves 104, 106. All the conducting elements 100, 101, 102, 103, 104, 106 are attached to the conductive dielectric material 44, which extends radially to, or possibly beyond the outermost radius of the conducting rings 104, 106. The conducting plates 100, 101 are connected to the electrical generator (not shown) via two electrical connections 110, 120 respectively. As in previous figures, for simplicity purposes, the backing material 78 is omitted. This backing material 78 would have been on top of the conducting plates, away from the pad side which would be in contact with the subject.

Figure 12:
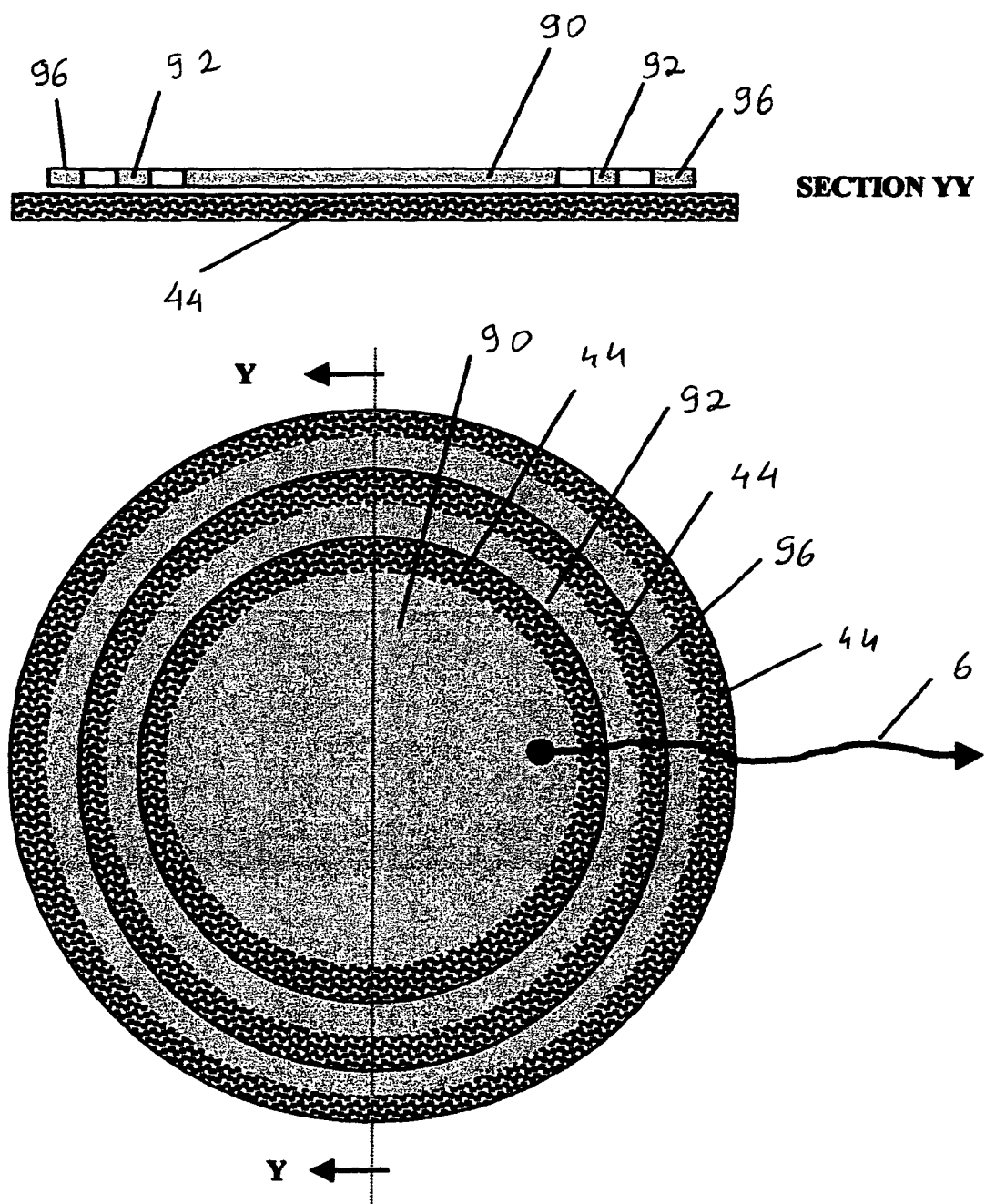
FIG. 12 provides top and cross sectional views of another example of a resistive-capacitive divider electrode of the present invention, namely a circular, three component (one central plate and, two rings), single (non-split) pad.

FIG. 12 shows both a bottom view and a cross sectional view YY of a single (non-split) version of three component (one central plate, two rings) dispersive pad shown in FIG. 11. In the single pad version shown, the central conducting plate is 90, the first conducting ring is 92, and the second conducting ring 96. All the conducting elements 90, 92, 96 are attached to the gel-like material 44, which can extend to, or beyond, the outermost radius of the conducting rings 96. The conducting plate 90 is connected to the electrical generator (not shown) via electrical connection 6. As in previous figures, for simplicity the electrically non-conductive backing material 78 is omitted. This electrically non-conductive backing material 78 would have been on top of the conducting plates, away from the pad side which would be in contact with the subject.

While the invention has been described so far with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. For example, the pads can take the shape of various geometries beyond those described in the figures; likewise, the edges of the conducting material can take the form of curved lines or waves, both on the inside and outside, segmented electrode and segmented conductive dielectric gel, or solid, with different electrical and thermal properties at each component or section; appropriate use of distributed circuit elements like conductive/dielectric layers (conductive gel or other conducting material including metallic foils); lumped (discrete) circuit elements placed on the subject side or the opposite side of the dispersive pad. Other variations are single and split-pads; circular and non-circular; symmetric and non-symmetric; disposable and non-disposable, or by combinations of these approaches. Furthermore, the distributed or lumped-element approach can be used effectively in accordance with category (1), category (2) and category (3) according to the principles of this invention.

Figure 13:
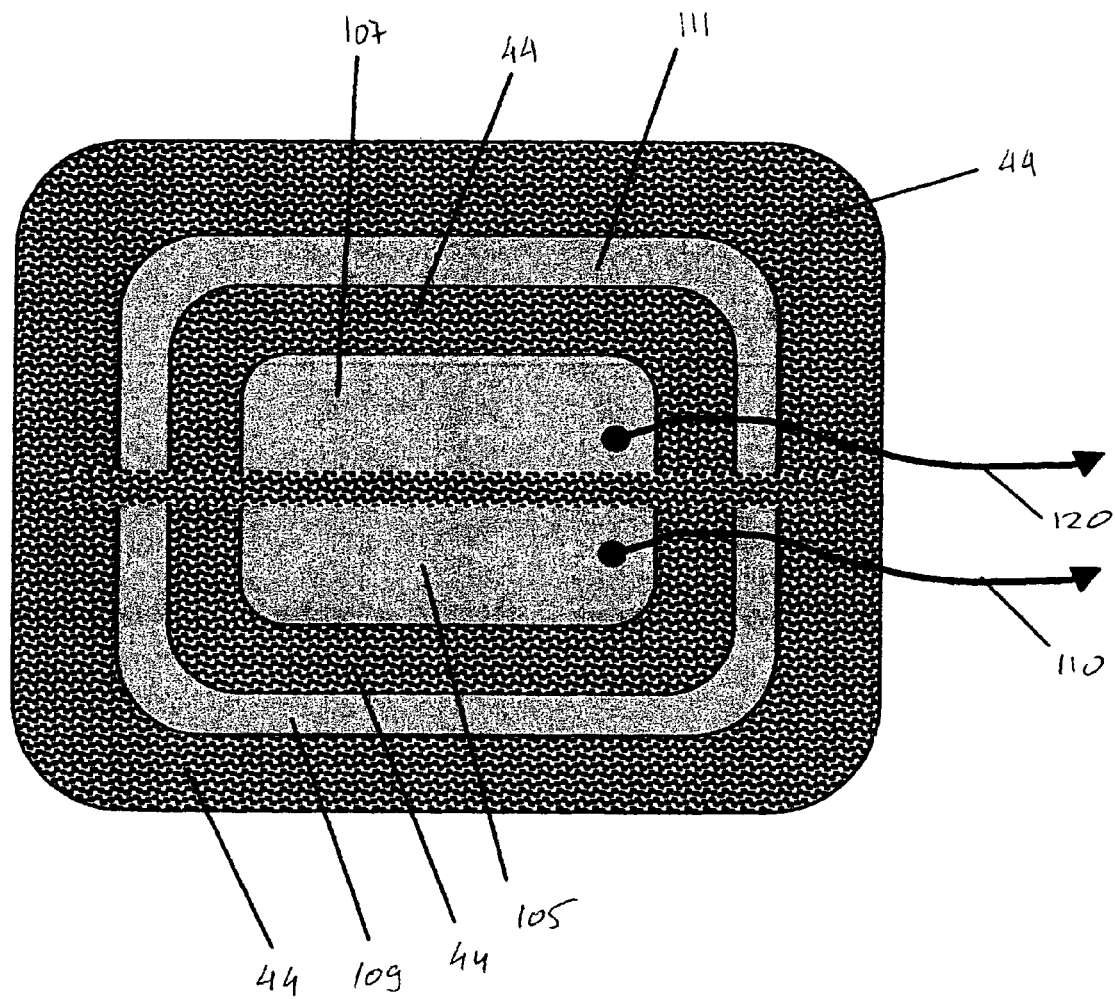
FIG. 13 provides top and cross sectional views of another example of a resistive-capacitive divider electrode of the present invention, namely a rectangular, two component (one central plate and one rectangular ring), split pad. Many other variations are contemplated, such as, multi-electrode and single (non-split) pads.
Figure 14:
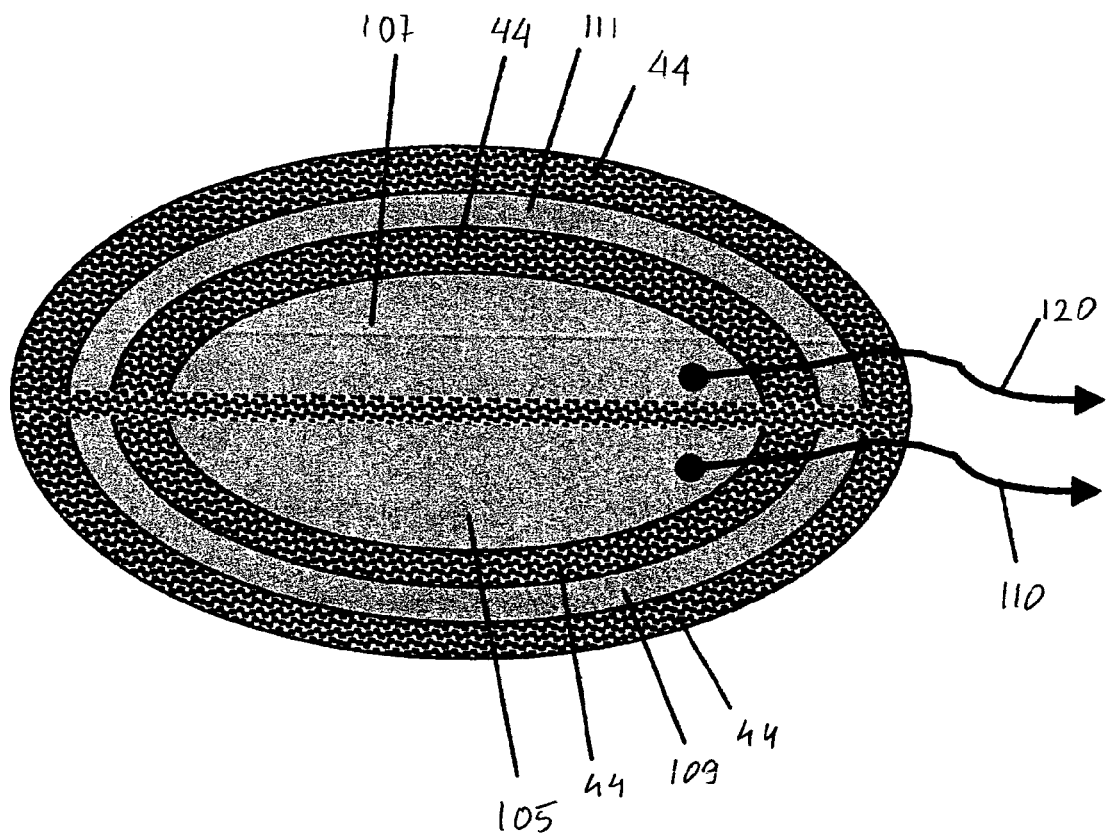
FIG. 14 provides top and cross sectional views of another example of a resistive-capacitive divider electrode of the present invention, namely an elliptical, two component (one central plate and one elliptical ring), split pad. Many other variations are contemplated, such as, multi-electrode and single (non-split) pads.

As indicated above, the dispersive electrodes can take the shape of various geometries beyond those described thus far, including circular and non-circular; symmetric and non-symmetric. FIGS. 13 and 14 illustrate two illustrative examples of non-circular embodiments. FIG. 13 shows a top view of a rectangular, two-component (one center plate, one rectangular ring) split pad according to the principles of category (1) of this invention (i.e., a resistive-capacitive divider). Many other variations are possible, including multi-component, multi-ring electrodes, as well as single (non-split) pads. Referring now to FIG. 13, the two central conducting elements 105, 107 are electrically connected to the external electrical source with two electrical conductors 110, 120. The two halves of rectangular conducting rings 109, 111, as well as the elements 105, 107 are mounted on material 44 which can extend to, or beyond, the outermost edges of the conducting elements 109, 111. The corners of all elements may be rounded, as shown in this figure, rectangular or any other shape. For simplicity, the backing material 78 is not visible in this figure.

FIG. 14 is a top view of yet another example of a device similar to that shown in FIG. 13, with the exception that the shape is elliptical. The two central conducting elliptical elements 105, 107 are electrically connected to an external electrical source with two electrical conductors 110, 120. The two halves of the elliptical conducting rings 109, 111, as well as the elements 105, 107 are mounted on, or glued to, the gel-like material 44 which can extend to, or beyond, the outermost radius of the conducting elements 109, 111. Again, for simplicity, the backing material 78 is not visible in FIG. 14.

FIGS. 15, 16, 17, 18, 19 illustrate yet other variations in accordance with the principles of this invention. The examples shown are in accordance with category (1) of this invention; however, similar variations equally apply to category (2) and category (3). It will be appreciated that the description is illustrative of the invention and is not constructed as limiting of the invention. Various modifications and applications may occur to those who are skilled in the art, without departing from the spirit and the scope of the invention, as described by the appended claims like multi-component, multi-ring electrodes; single (non-split) and split pads; symmetric and non-symmetric; disposable and non-disposable, uniform and non-uniform thickness of gel-like material.

Figure 15:
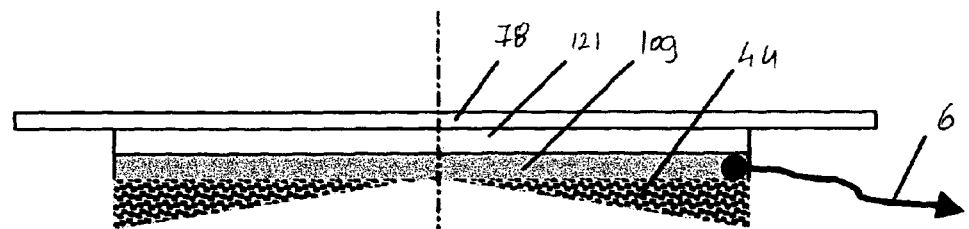
FIG. 15 provides a cross sectional view of another example of a resistive-capacitive divider electrode of the present invention, including a non-segmented return pad.

FIG. 15 is cross sectional view of a non-segmented return electrode according to the principles of category (1) of this invention. The conductive dielectric intermediate layer 44 between the conducting element 109 and of the subject tissue 43, not shown, is applied with a thickness increasing smoothly from the center of the device toward its outer edge, covering the entire area of the conducting element 109. The conducting element 109 is connected to the return or neutral or ground terminal of the electrical unit. The conducting element 109 may be attached, or glued, to the backing material 78 with a field of glue 121. The material 44 extend radially to the edge of the conducting element 109.

Figure 16:
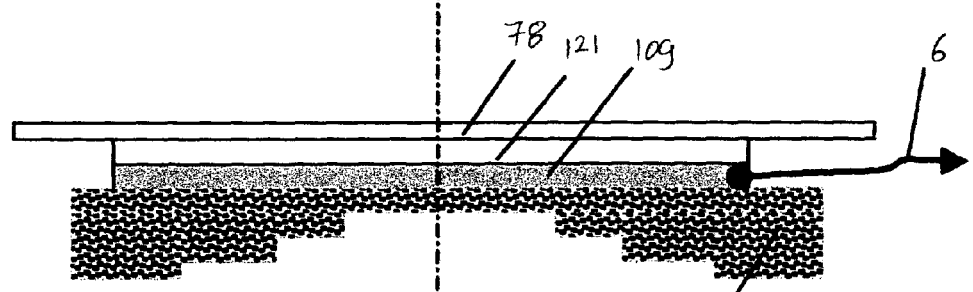
FIG. 16 provides a cross sectional view of another example of a resistive-capacitive divider electrode of the present invention, including a non-segmented return pad.

Another variation of non-uniform application of the conductive dielectric intermediate layer 44 is illustrated in FIG. 16, which is cross sectional view of a non-segmented return electrode according to the principles of category (1) of this invention. The intermediate layer 44 between the conducting element 109 and of the subject tissue 43, not shown, is applied with a thickness increasing in steps toward the outer edge of the device, covering part, or all, area of the conducting element 109. The field 44 can extend to, or beyond, the outermost radius of the conducting element 109. The conducting element 109 is connected to the return or neutral or ground terminal of the electrical unit. The conducting element 109 may be attached, or glued, to the backing material 78 with a field of glue 121.

Figure 17:
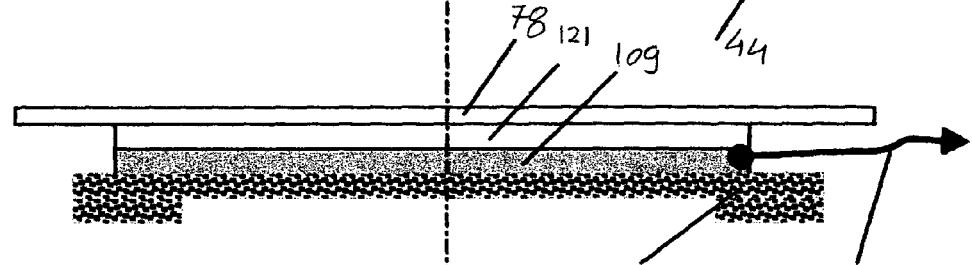
FIG. 17 provides a cross sectional view of another example of a resistive-capacitive divider electrode of the present invention, including a non-segmented return pad.

Yet another variation of non-uniform application of the intermediate layer 44 is illustrated in FIG. 17, which is cross sectional view of a non-segmented return electrode according to the principles of category (1) of this invention. The intermediate layer 44 between the conducting element 109 and of the subject tissue 43, not shown, is applied with a uniform thickness up to a certain radius and then increases in one step toward the outer edge of the device, covering part, or all, area of the conducting element 109. The field 44 can extend to, or beyond, the outermost radius of the conducting element 109. The conducting element 109 is connected to the return or neutral or ground terminal of the electrical unit. The conducting element 109 may be attached, or glued, to the backing material 78 with a field of glue 121.

Figure 18:
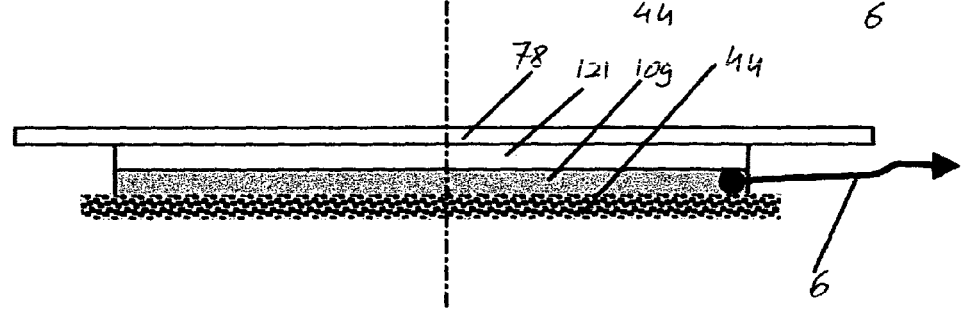
FIG. 18 provides a cross sectional view of another example of a resistive-capacitive divider electrode of the present invention, including a non-segmented return pad.

Yet another variation of uniform application of the intermediate layer 44 is illustrated in FIG. 18, which is cross sectional view of a non-segmented return electrode according to the principles of category (1) of this invention. The intermediate layer 44 between the conducting element 109 and of the subject tissue 43, not shown, is applied with a uniform thickness covering part, or all, area of the conducting element 109. The field 44 can extend to, or beyond, the outermost radius of the conducting element 109. The conducting element 109 is connected to the return or neutral or ground terminal of the electrical unit. The conducting element 109 may be attached, or glued, to the backing material 78 with a field of glue 121.

Figure 19:
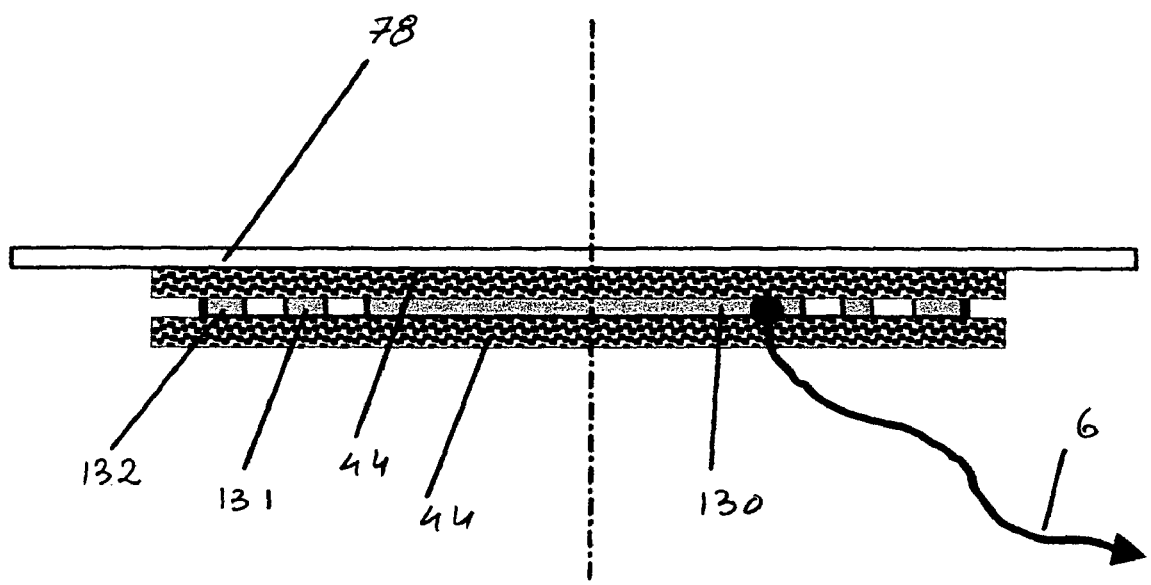
FIG. 19 provides a cross sectional view of another example of a resistive-capacitive divider electrode of the present invention, including a segmented return pad.

FIG. 19 is cross sectional view of yet another possible variation, which shows a single (non-split) three-component (one center plate, two-rings) device, similar to the device shown in FIG. 12, with the difference being that the conductive dielectric layer 44 attached on both sides of the conducting electrodes 130, 131, 132. The central conducting element 130, as well as the first conducting ring 131 and the second conducting ring 132 are sandwiched between two layers of the intermediate material 44. One layer of 44 is attached to the backing material 78. The second layer of 44 is attached to the subject skin or tissue. The central conducting element 130 is connected to the return or neutral or ground terminal of the electrical unit with an electrical wire 6.

FIGS. 20, 21, 22, 23, 24, 25, 26 depict illustrative examples in accordance with category (2) of this invention, i.e., a passive resistive-inductive divider. It will be appreciated that the description is illustrative of the invention and is not constructed as limiting of the invention. Various modifications and applications may occur to those who are skilled in the art, without departing from the spirit and the scope of the invention, as described by the appended claims like multi-component electrodes; single (non-split) and split pads; symmetric and non-symmetric; disposable and non-disposable, uniform and non-uniform thickness of gel-like material.

Figure 20:
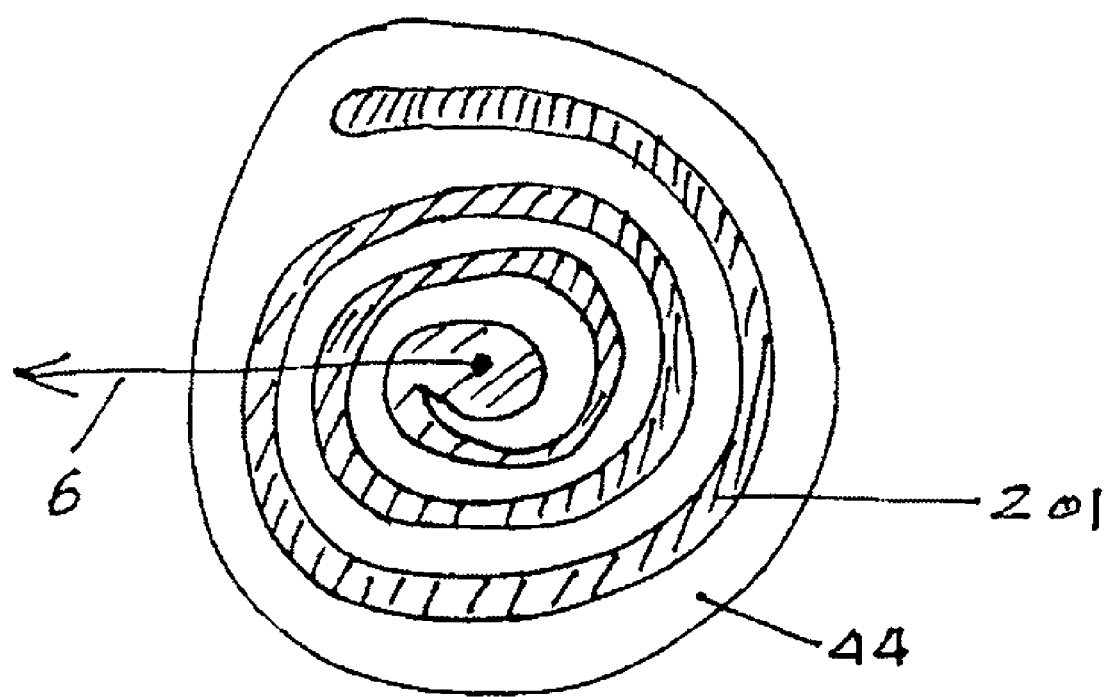
FIG. 20 provides a top view of a resistive-inductive divider electrode of the present invention, namely a single (non-split), single-spiral return electrode.

A top view of non-split device, with an electrically conducting element 201 in a form of a single spiral, according to the principles of category (2) of this invention is illustrated in FIG. 20. The intermediate layer 44 between the conducting element 201 and of the subject tissue 43, not shown, is applied with either a uniform, or non-uniform, thickness covering part, or all, area of the spiral conducting element 201. The field 44 can extend to, or beyond, the outermost radius of the conducting element 201. The center of the conducting element 201 is connected to the return or neutral or ground terminal of the electrical unit with an electrical wire 6. The conducting element 201 may be attached, or glued, to the backing material 78, not shown in this figure.

Figure 21:
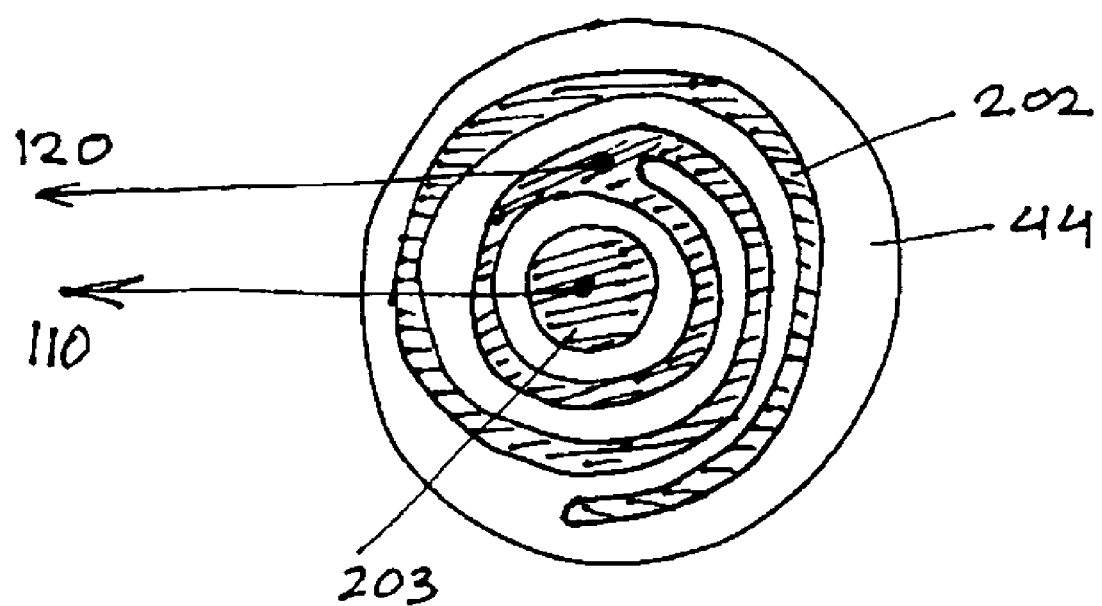
FIG. 21 provides a top view of another example of a resistive-inductive divider electrode of the present invention, namely a split, single-spiral return electrode.

FIG. 21 depicts a top view of a split pad, with an electrically conducting element 202 in a form of a single spiral and a center conducting element 203, according to the principles of category (2) of this invention. The intermediate layer 44 between the conducting elements 202, 203 and of the subject tissue 43, not shown, is applied with either a uniform, or non-uniform, thickness. The field 44 can extend to, or beyond, the outermost radius of the conducting element 202. The conducting elements 202, 203 are connected to the electrical unit with electrical wires 120, 110. The conducting elements 203, 202 may be attached, or glued, to the backing material 78, not shown in this figure.

Figure 22:
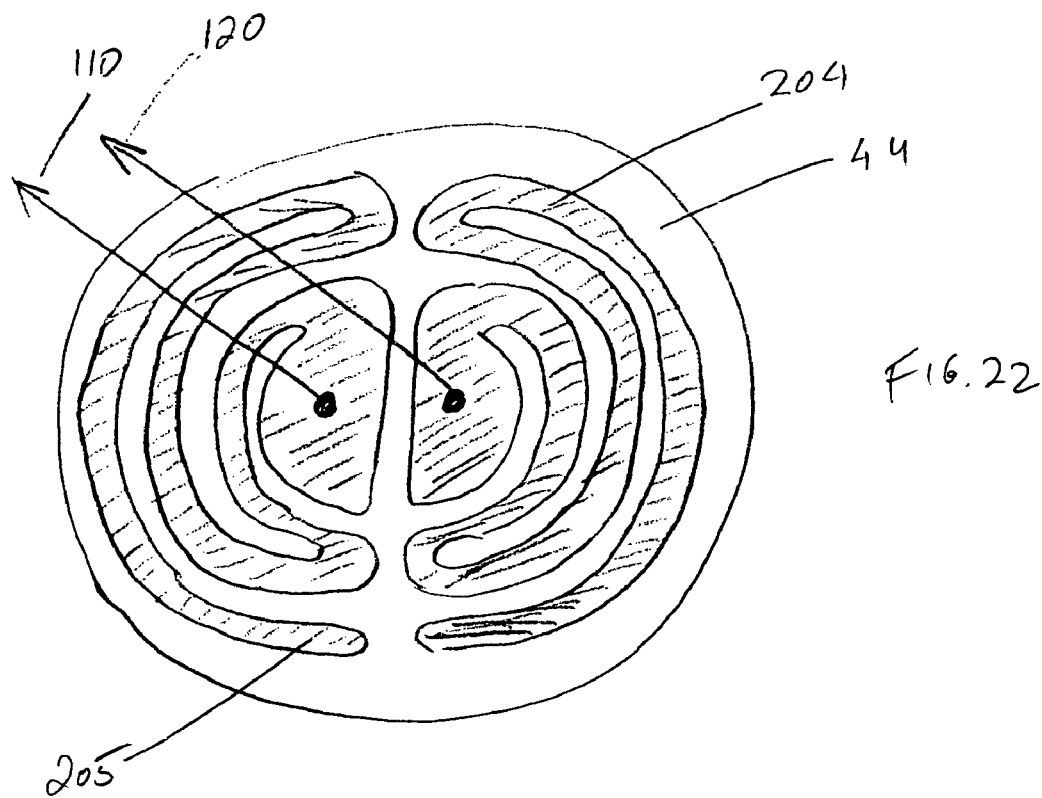
FIG. 22 provides a top view of another example of a resistive-inductive divider electrode of the present invention, namely a split, double-spiral return electrode.

FIG. 22 shows a top view of a yet another version of a split pad, with two electrically conducting elements 204, 205 in the form of symmetric split spirals, according to the principles of category (2) of this invention. The intermediate layer 44 between the conducting elements 204, 205 and of the subject tissue 43, not shown, is applied with either a uniform, or non-uniform, thickness. The field 44 can extend to, or beyond, the outermost radius of the conducting element 204, 205. The conducting elements 205, 204 are connected to the electrical unit with electrical wires 120, 110 as shown. The conducting elements 204, 205 may be attached, or glued, to the backing material 78, not shown in this figure.

Figure 23:
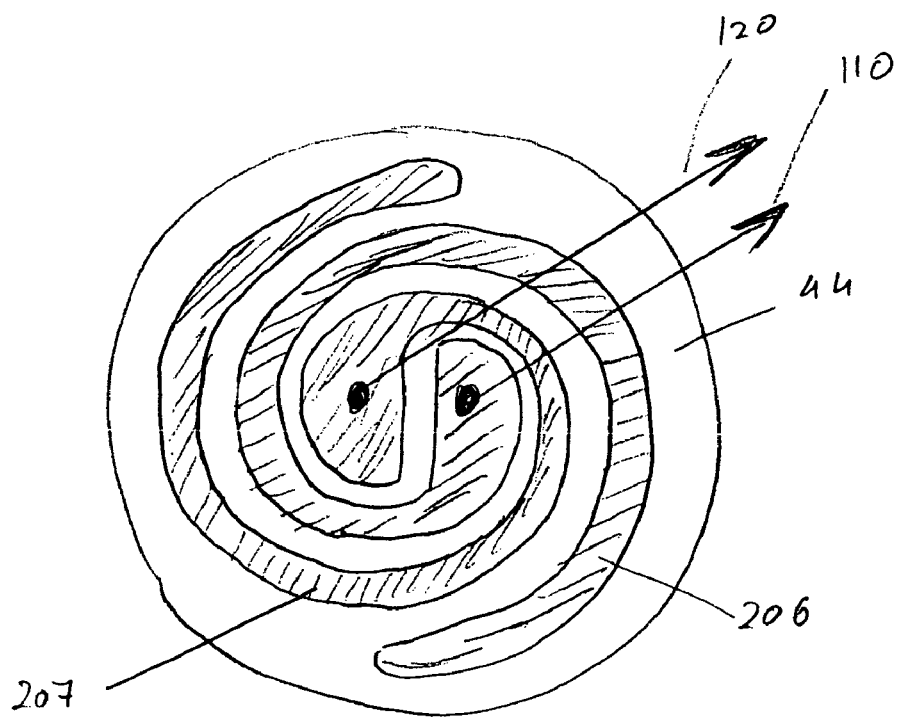
FIG. 23 provides a top view of another example of a resistive-inductive divider electrode of the present invention, namely a split, double-spiral return electrode.

FIG. 23 shows a top view of a yet another version of a split pad, with two electrically conducting elements 206, 207 in the form of nested spirals, according to the principles of category (2) of this invention. The intermediate layer 44 between the conducting elements 206, 207 and of the subject tissue 43, not shown, is applied with either a uniform, or non-uniform, thickness. The field 44 can extend to, or beyond, the outermost edges of the conducting element 206, 207. The conducting elements 206, 207 are connected to the electrical unit with electrical wires 110, 120 as shown. The conducting elements 206, 207 may be attached, or glued, to the backing material 78, not shown in this figure.

Figure 24:
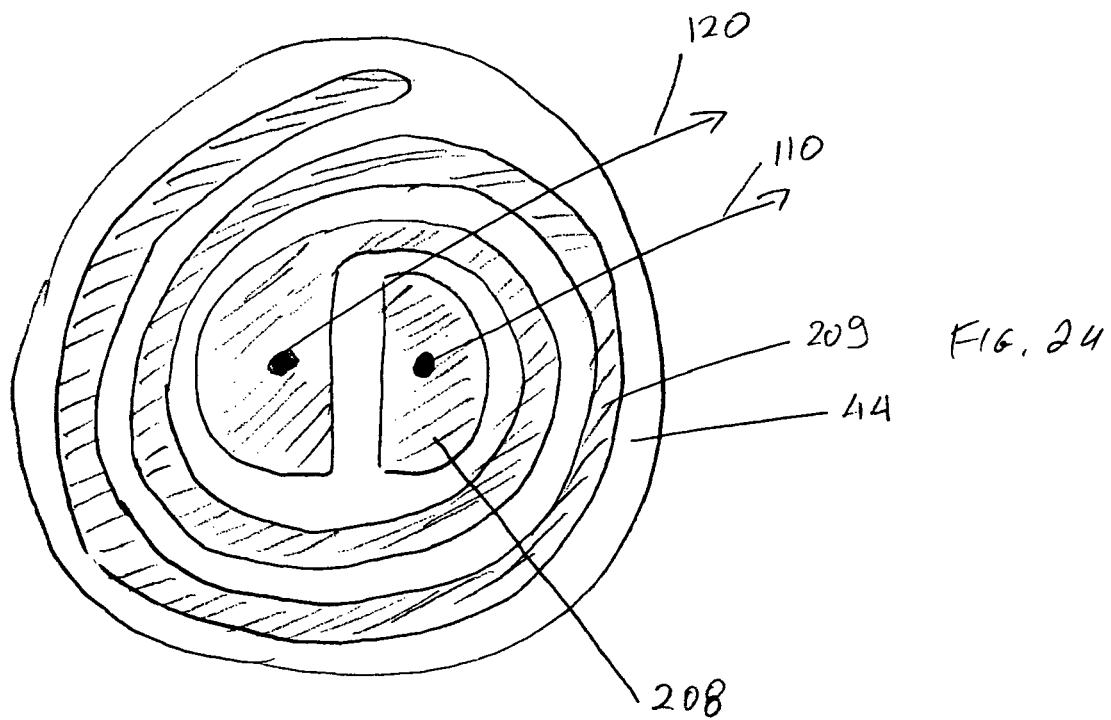
FIG. 24 provides a top view of another example of a resistive-inductive divider electrode of the present invention, namely a split, single-spiral return electrode.

FIG. 24 shows a top view of a yet another version of a split pad, with two electrically conducting elements 208, 209 according to the principles of category (2) of this invention. Conducting element 209 can be in form of a spiral, as shown in the figure. The intermediate layer 44 between the conducting elements 208, 209 and of the subject tissue 43, not shown, is applied with either a uniform, or non-uniform, thickness. The field 44 can extend to, or beyond, the outermost radius of the conducting element 209. The conducting elements 208, 209 are connected to the electrical unit with electrical wires 110, 120 as shown. The conducting elements 208, 209 may be attached, or glued, to the backing material 78, not shown in this figure.

Figure 25:
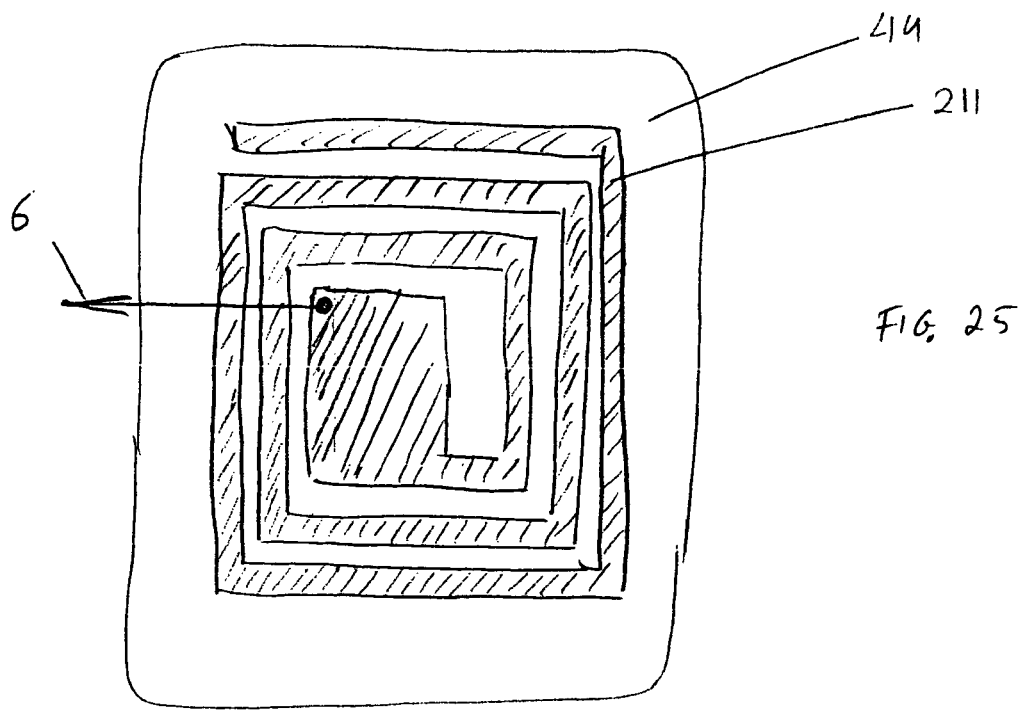
FIG. 25 provides a top view of another example of a resistive-inductive divider electrode of the present invention, namely a single, rectangular single-spiral return electrode.

FIG. 25 shows a top view of a yet another version of a single, non-split pad, with one conducting element 211 according to the principles of category (2) of this invention. Conducting element 211 can be in form of a rectangular spiral, as shown in the figure. The intermediate layer 44 between the conducting element 211 and of the subject tissue 43, not shown, is applied with either a uniform, or non-uniform, thickness. The field 44 can extend to, or beyond, the outermost edge of the conducting element 211. The conducting element 211 is connected to the electrical unit with electrical wires 6 as shown. The conducting elements 211 may be attached, or glued, to the backing material 78, not shown in this figure.

Figure 26:
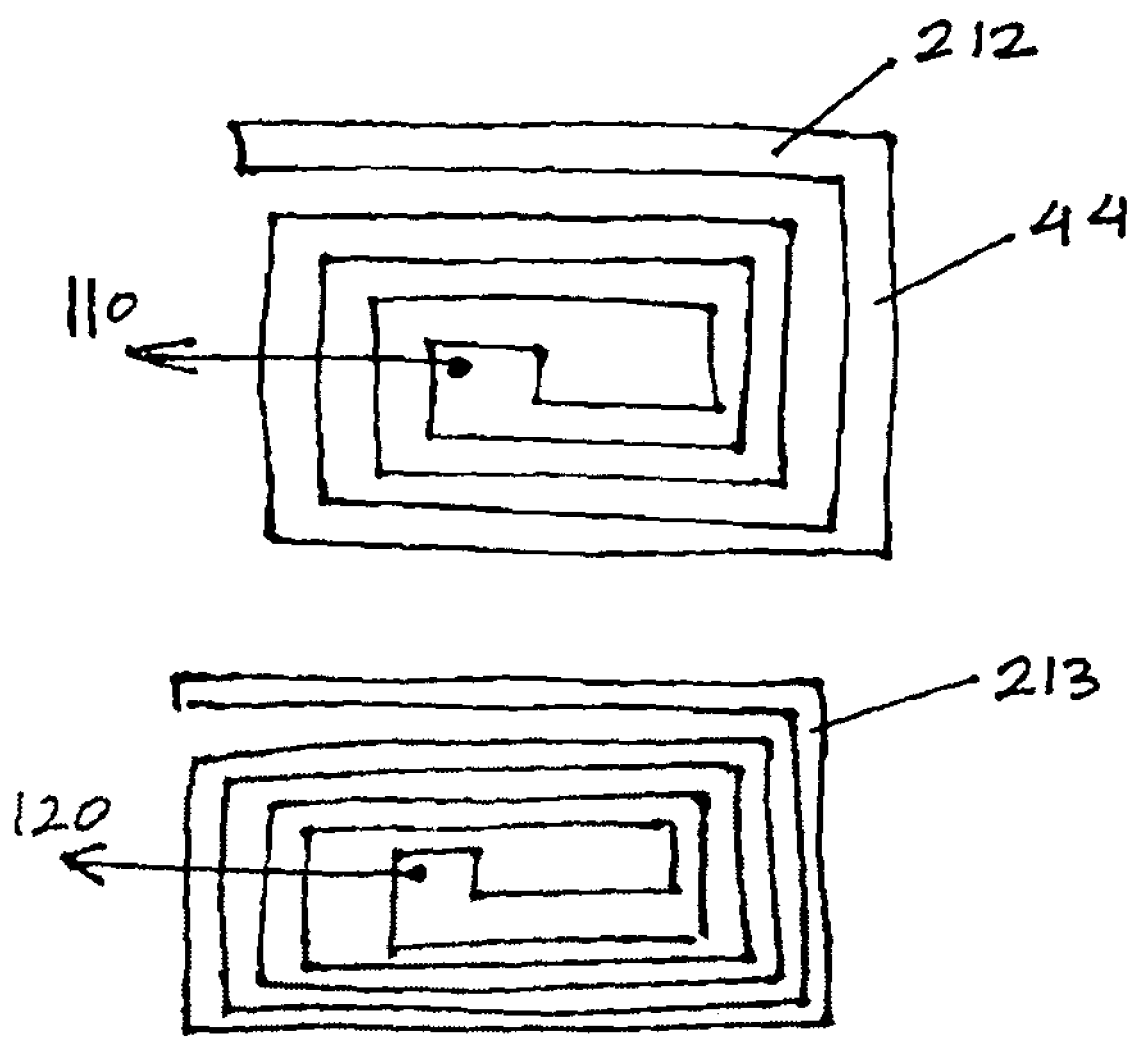
FIG. 26 provides a top view of another example of a resistive-inductive divider electrode of the present invention, namely a split, rectangular double spiral return electrode.

FIG. 26 depicts yet another version of a split pad with two conducting elements 212, 213 according to the principles of category (2) of this invention. The conducting elements 212, 213 can be in the form of a pair of rectangular spirals, as shown in the figure. As noted previously, the conductive spiral may be in the form of other geometries such as circles, ellipses, polygons, and combinations thereof, both symmetric and non-symmetric. The intermediate layer 44 between the conducting elements 212, 213 and of the subject tissue 43, not shown, is applied with either a uniform, or non-uniform, thickness. The field 44 can extend to, or beyond, the outermost edge of the conducting elements 212, 213. The conducting elements 212, 213 are connected to the electrical unit with electrical wires 110, 120 as shown. The conducting elements 212, 213 may be attached, or glued, to the backing material 78, not shown in this figure.

Figure 27:
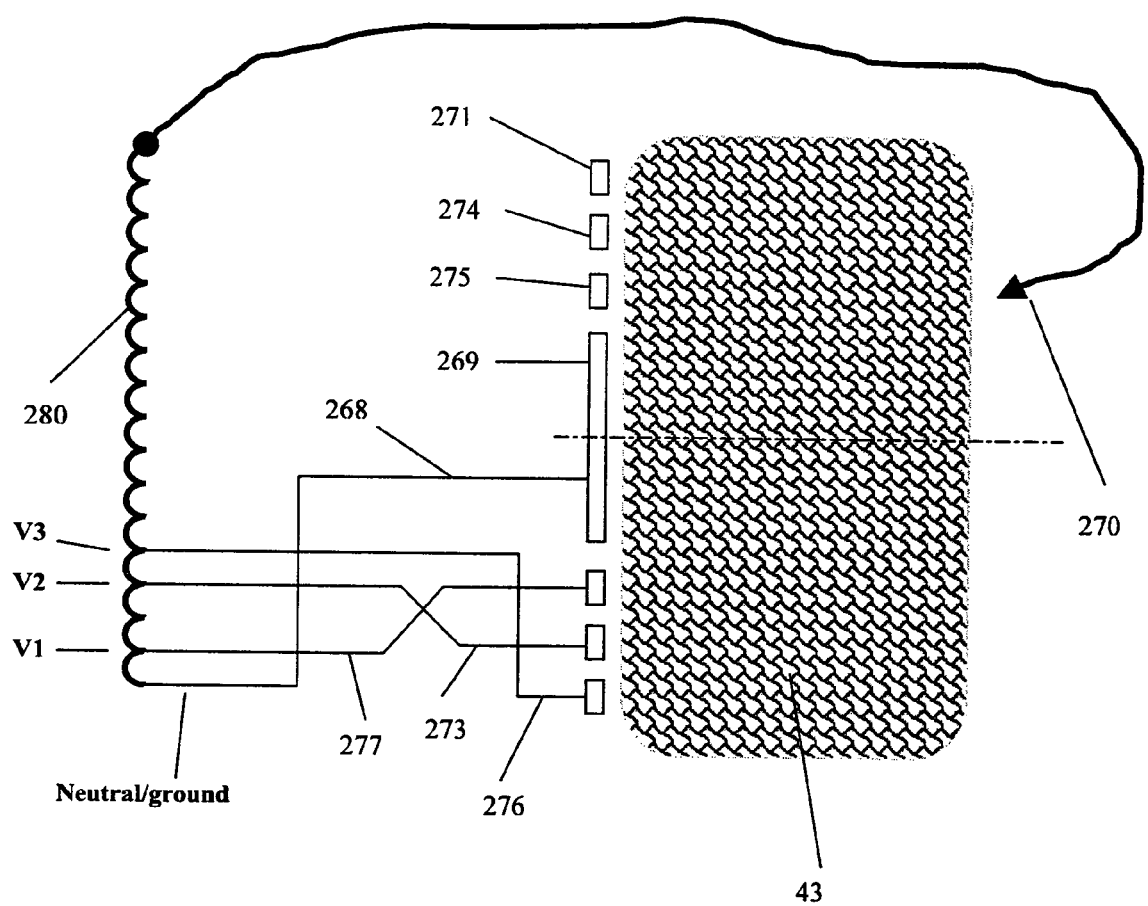
FIG. 27 provides a schematic diagram for a system for active voltage distribution according to the present invention. Herein, a favorable voltage distribution on the return electrode is created by supplying voltages from an external source.

FIG. 27 illustrates an example for implementing a system for active voltage distribution in accordance with category (3) of this invention, i.e., an active voltage distribution. Here, the favorable voltage distribution on the electrode is created by supplying the desired voltages from external sources, as opposed to a self generated voltage distribution by using resistive-capacitive or resistive-inductive lumped or distributed elements as described above. The particular example shown in FIG. 27, represents a single (non-split), four component (one central plate, three-rings) dispersive pad 43 based on active voltage distribution. External voltage source, schematically represented by a transformer 280, generates voltages V1, V2 and V3, supplied to the conducting components—central conducting plate 269 and concentric rings 271, 274 and 275—with electrical wires 270, 277, 273 and 276 respectively, with the neutral/ground wire represinted by element 268.

Figure 28:
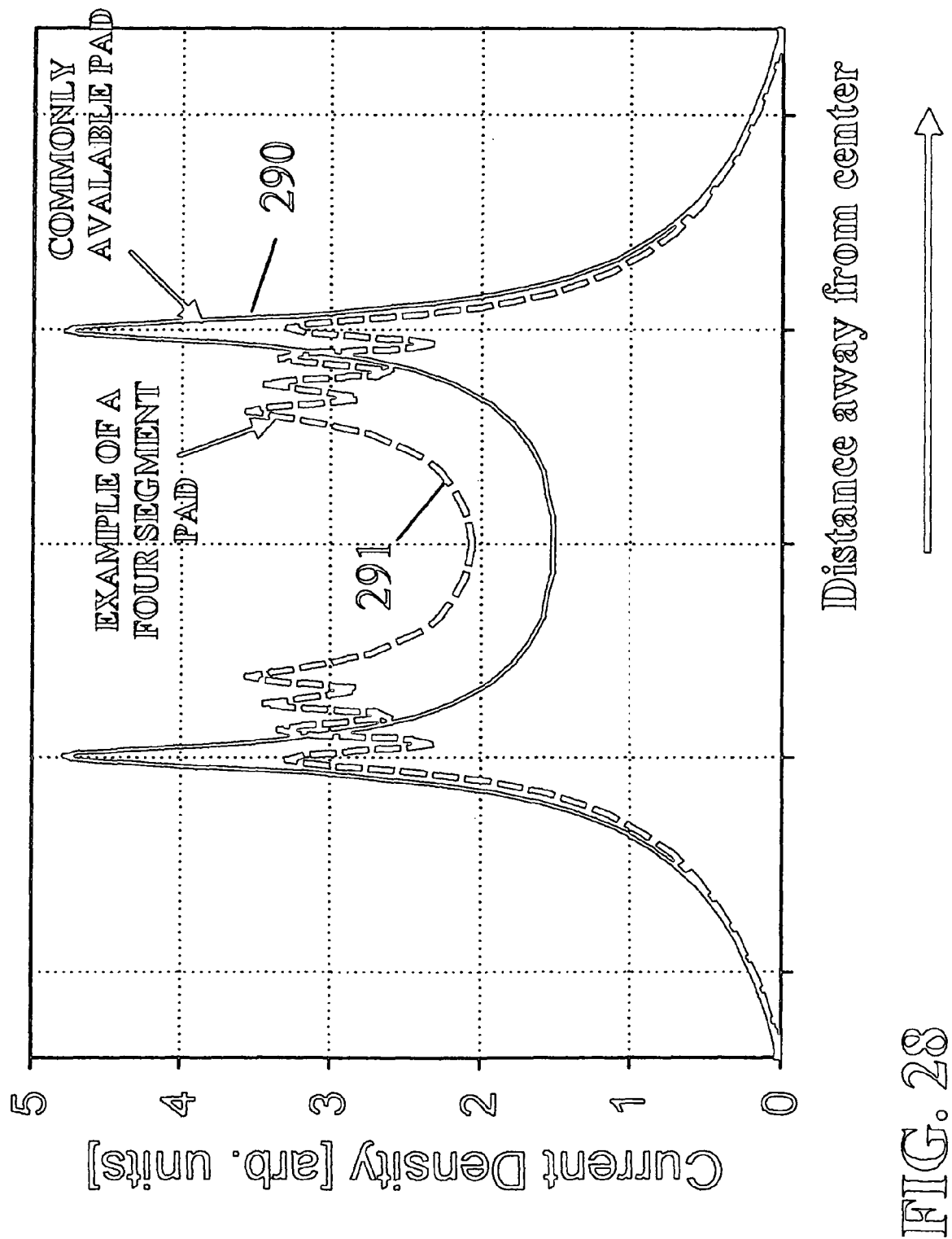
FIG. 28 is an illustration depicting the calculated current density distribution over a circular return electrode designed based on principles of known prior art, and that of a four component (one central plate and, three rings) return electrode according to the principles of this invention. Note that with the prior art pad, the current distribution is highly non-uniform and tends to cluster in the vicinity of the edge, but the distribution is much more uniform for a pad designed according to the principles of this invention.

The invention is further described by way of a specific example shown in FIG. 28. It shows the calculated current density distribution over a circular return electrode designed based on principles of known prior art 290, and the calculated current density distribution 291 over a four component, three ring circular return electrode designed based on the principles of active voltage distribution according to the principles of this invention. Note that with the prior art pad, the current distribution is highly non-uniform and tend to cluster in the vicinity of the edges, but the distribution is much more uniform for a pad designed according to the principles of this invention.

While the invention has been described in detail and with reference to specific embodiments thereof, it will be apparent to one skilled in the art that various changes and modifications can be made therein without departing from the spirit and scope of the invention. For example, various modifications and applications may occur to those who are skilled in the art, without departing from the spirit and the scope of the invention, as described by the appended claims like multi-component electrodes; single (non-split) and split pads; symmetric and non-symmetric; disposable and non-disposable, uniform and non-uniform thickness of conductive dielectric material; combinations of categories (1), (2) and (3) described above, as well as various combinations of active and passive approaches for generating voltage distributions.

All publications, patent applications, patents and other references mentioned herein are incorporated by reference in their entirety.

What is claimed:

1. A biomedical electrode adapted for use in combination with an electrical generator said electrode comprising:
    a. a layer of conductive dielectric;
    b. a series of discrete electrical conductors mounted to one side of said conductive dielectric layer, said series comprising one or more inner conductors and at least one outer conductor; and
    c. one or more electrical connections for connection to the electrical generator to establish a return current thereto, wherein said electrical connections are attached exclusively to the innermost of said one or more inner conductors, further wherein said biomedical electrode provides a relatively uniform radial redistribution of current at a subject contacting surface.

2. The biomedical electrode of claim 1, wherein said conductive dielectric has an electrical resistivity ranging from 0.1 to 200 ohm·m.

3. The biomedical electrode of claim 2, wherein said electrical resistivity ranges from 1 to 20 ohm·m.

4. The biomedical electrode of claim 1, wherein said electrode comprises a passive dispersive electrode that collects current induced in the body of the subject by said electrical generator.

5. The biomedical electrode of claim 1, wherein said electrode comprises a thin, flexible pad adapted to conform to the body of the subject.

6. The biomedical electrode of claim 1, further comprising an electrically non-conductive backing layer disposed over said electrical conductors, opposite said layer of conductive dielectric.

7. The biomedical electrode of claim 6, further comprising a film of adhesive adhering said electrical conductors to said backing layer.

8. The biomedical electrode of claim 1, wherein said conductive dielectric layer comprises a conducting gel that conforms to the shape of the subject's body.

9. The biomedical electrode of claim 1, wherein the outer edges of said conductive dielectric layer extend beyond a perimeter defined by said conductors.

10. The biomedical electrode of claim 1, wherein the outer edges of said electrical conductors are curvilinear or waved.

11. The biomedical electrode of claim 1, wherein said conductive dielectric layer is of non-uniform thickness.

12. The biomedical electrode of claim 11, wherein the thickness of said conductive dielectric layer increases from its center point to its outer edges.

13. The biomedical electrode of claim 11, wherein the thickness of said conductive dielectric layer smoothly tapers from a first thickness at its outer edge to a reduced second thickness at its center point.

14. The biomedical electrode of claim 11, wherein the thickness of said conductive dielectric layer decreases in a stepwise fashion from a first thickness at its outer edge to a reduced second thickness at its center point.

15. The biomedical electrode of claim 1, further comprising an additional layer of conductive dielectric material disposed over said electrical conductors such that the electrical conductors are sandwiched between two layers of conductive dielectric material.

16. The biomedical electrode of claim 1, further comprising one or more lumped circuit elements electrically connecting said discrete conductors, said circuit elements disposed on the side of said conductors opposite to said conductive dielectric layer.

17. The biomedical electrode of claim 16, wherein said lumped circuit elements are selected from the group consisting of resistors, capacitors, inductors and combinations thereof.

18. The biomedical electrode of claim 1, wherein said one or more electrical connections comprises an insulated wire.

19. The biomedical electrode of claim 1, wherein said electrical conductors are symmetrically disposed about the center of said conductive dielectric layer.

20. The biomedical electrode of claim 1, wherein said electrical conductors comprise a central plate surrounded by one or more concentric rings.

21. The biomedical electrode of claim 20, wherein the shape of said central plate and its corresponding concentric rings is selected from the group consisting of a circle, an ellipse, a rectangle, a square, a polygon and symmetric and non-symmetric combinations thereof.

22. The biomedical electrode of claim 20, wherein said central plate and/or one or more of said concentric rings is split into two discrete halves.

23. The biomedical electrode of claim 22, wherein said electrode comprises two electrical connections, a first connection attached to a first half of said central plate and a second connection attached to a second half of said central plate.

24. The biomedical electrode of claim 20, wherein said concentric rings are connected to each other so as to form a multi-turn spiral.

25. A biomedical electrode adapted for use in combination with an electrical generator said electrode comprising:
   a. a layer of conductive dielectric;
   b. a plurality of electrical conductors mounted to one side of said conductive dielectric layer, said plurality comprising one or more inner conductors and at least one outer conductor; and
   c. one or more electrical connections for connection to the electrical generator to establish a return current thereto,
   wherein said electrical connections are attached exclusively to the innermost of said one or more inner conductors, further wherein said biomedical electrode provides a relatively uniform radial redistribution of current at a subject contacting surface, further wherein the outer edges of said conductive dielectric layer extend beyond a perimeter defined by said one or more electrical conductors.

26. The biomedical electrode of claim 25, wherein the outer edges of said electrical conductors are curvilinear or waved.

27. The biomedical electrode of claim 25, wherein said conductive dielectric layer is of non-uniform thickness.

28. The biomedical electrode of claim 27, wherein the thickness of said conductive dielectric layer increases from its center point to its outer edges.

29. The biomedical electrode of claim 27, wherein the thickness of said conductive dielectric layer smoothly tapers from a first thickness at its outer edge to a reduced second thickness at its center point.

30. The biomedical electrode of claim 27, wherein the thickness of said conductive dielectric layer decreases in a stepwise fashion from a first thickness at its outer edge to a reduced second thickness at its center point.

31. The biomedical electrode of claim 25, further comprising an additional layer of conductive dielectric material disposed over said electrical conductors such that the electrical conductors are sandwiched between two layers of conductive dielectric material.

32. The biomedical electrode of claim 25, said plurality of electrical conductors is symmetrically disposed about the center of said conductive dielectric layer.

33. The biomedical electrode of claim 25, wherein said plurality of electrical conductors comprises a central plate surrounded by one or more concentric rings.

* * * * *